(12) United States Patent
Harris et al.

(10) Patent No.: US 6,407,259 B1
(45) Date of Patent: Jun. 18, 2002

(54) PROCESS FOR THE PREPARATION OF PYRAZOLES

(75) Inventors: Laurence James Harris; Philip Charles Levett, both of County of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/900,097

(22) Filed: Jul. 6, 2001

Related U.S. Application Data
(60) Provisional application No. 60/231,430, filed on Sep. 8, 2000, and provisional application No. 60/290,737, filed on May 14, 2001.

(30) Foreign Application Priority Data

Jul. 28, 2000 (GB) .............................................. 0018662
Mar. 14, 2001 (GB) .............................................. 0106276

(51) Int. Cl.[7] ...................... C07D 231/10; C07D 403/00
(52) U.S. Cl. ................ 548/364.1; 548/366.1; 548/367.4; 548/370.1; 548/370.4
(58) Field of Search .......................... 548/364.1, 366.1, 548/367.4, 370.1, 370.4

(56) References Cited

U.S. PATENT DOCUMENTS

| | | | |
|---|---|---|---|
| 4,666,921 A | * | 5/1987 | Herter et al. ................. 514/326 |
| 5,808,092 A | * | 9/1998 | Mizutare et al. .......... 548/366.1 |
| 6,015,911 A | * | 1/2000 | Siddall et al. ............ 548/369.4 |

FOREIGN PATENT DOCUMENTS

| | | | |
|---|---|---|---|
| EP | 0463756 | 1/1992 | |
| EP | 0812845 | 4/1997 | ......... C07D/487/04 |
| EP | 0994115 | 11/1999 | ......... C07D/487/04 |
| EP | 0995750 | 4/2000 | |
| WO | WO 9849166 | 11/1998 | ......... C07D/487/04 |
| WO | WO 9954333 | 10/1999 | ......... C07D/487/04 |
| WO | WO 0127112 | 4/2001 | |
| WO | WO 0127113 | 4/2001 | |

OTHER PUBLICATIONS

Martins, M.A.P.; Freitag, R.; Flores, A.F.C.; Zanatta, N. Synthesis, 1995, 1491.
Martins, M.A.P.; Flores, A.F.C.; Zanatta, N.; Bastos, G.P.; Bonacorso, H.G.; Siqueira, G.M.; Tetrahedron Letters, 1999, 40, 4309.
Seki, Kunio, et al.; Studies on Hypolipidemic Agents. II[1]) Synthesis and Pharmacological Properties of Alkylpyrazole Derivatives[2)].; Chem. Pharm. Bull., 32(4) pp. 1568–1577, (1984).

* cited by examiner

Primary Examiner—Floyd D. Higel
Assistant Examiner—Golam M. M. Shameem
(74) Attorney, Agent, or Firm—Peter C. Richardson; Gregg C. Benson; Arlene K. Musser

(57) ABSTRACT

A "one-pot" process is described herein for the production of pyrazole compounds of general formula (II)

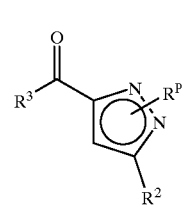

comprising the steps of reacting a compound of general formula (III)

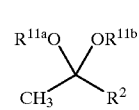

with an acylating agent in the presence of a base and an optional activating agent followed by the addition of a hydrazine compound in situ.

11 Claims, No Drawings

PROCESS FOR THE PREPARATION OF PYRAZOLES

This application claims the benefit of U.S. Provisional Patent Application Nos. 60/231,430 filed Sep. 8, 2000 and 60/290,737 filed May 14, 2001, both of which are incorporated herein by reference.

FIELD OF THE INVENTION

This invention relates to a novel process for the preparation of pyrazoles. In particular the present invention relates to a novel process for the preparation of pyrazole intermediates useful in the synthesis of 4-alkylpiperazinylsulfonylphenyl- and 4-alkylpiperazinylsulfonyl pyridinyl-dihydropyrazolo[4,3-d]pyrimidin-7-one derivatives which are potent and selective cGMP $PDE_5$ inhibitors.

BACKGROUND

A general synthetic route for the preparation of 4-alkylpiperazinylsulfonylphenyl-dihydropyrazolo[4,3-d]pyrimidin-7-one derivatives is described in EP 812 845, EP 994 115 and WO98/49166, and for analogues thereof is described in WO 99/54333. The synthesis involves a coupling reaction between an intermediate pyrazole compound and a phenyl or pyridinyl derivative followed by cyclization of the resulting coupled intermediate to provide pyrimidin-7-ones. Synthetic routes for the preparation of certain pyrazole compounds are also described in Martins, M. A. P.; Freitag, R.; Flores, A. F. C.; Zanatta, N. *Synthesis*, 1995, 1491 and Martins, M. A. P.; Flores, A. F. C.; Zanatta, N.; Bastos, G. P.; Bonacorso, H. G.; Siqueira, G. M. *Tetrahedron Lett.* 1999, 40,4309. In this processes the pyrazole compounds are prepared in two steps.

SUMMARY

According to a first aspect of the invention, there is provided a novel "one-pot" process for the production of pyrazole compounds of formula (II)

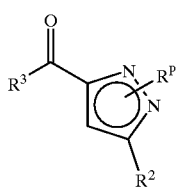

II wherein $R^P$ is H or $R^1$;

$R^1$ is H, $(C_1-C_6)$alkyl, $(C_1-C_6)$alkoxy, $(C_3-C_6)$cycloalkyl, $(C_1-C_6)$alkyl$((C_1-C_6)$alkoxy), Het, $(C_1-C_6)$alkylHet, aryl, or $(C_1-C_6)$alkylaryl, which latter eight groups are all optionally substituted by one or more substituents selected from the group consisting of halo, cyano, nitro, $(C_1-C_6)$alkyl, $C(O)NR^4R^5$, $C(O)R^6$, $C(O)OR^7$, $OR^8$, $NR^{9a}R^{9b}$ and $SO_2NR^{10a}R^{10b}$;

$R^2$ is $(C_1-C_6)$alkyl, $(C_1-C_6)$alkoxy, $(C_3-C_6)$cycloalkyl, $(C_1-C_6)$alkyl$((C_1-C_6)$alkoxy), Het, $(C_1-C_6)$alkylHet, aryl, or $(C_1-C_6)$alkylaryl, which latter eight groups are all optionally substituted by one or more substituents selected from the group consisting of halo, cyano, nitro, $(C_1-C_6)$alkyl, $C(O)NR^4R^5$, $C(O)R^6$, $C(O)OR^7$, $OR^8$, $NR^{9a}R^{9b}$ and $SO_2NR^{10a}R^{10b}$;

$R^3$ is OH, $(C_1-C_6)$alkoxy, or $NR^4R^5$;

$R^4$, $R^5$, $R^6$, $R^7$, $R^8$, $R^{10a}$ and $R^{10b}$ are each independently H or $(C_1-C_6)$alkyl;

$R^{9a}$ and $R^{9b}$ are each independently H, $(C_1-C_6)$alkyl, or taken together with the nitrogen atom to which they are attached form an azetidinyl, pyrollidinyl, or piperidinyl group;

wherein said process comprises the steps of (i) reacting a compound of formula (III)

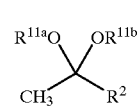

III where $R^{11a}$ and $R^{11b}$ are each independently $(C_1-C_6)$alkyl, $R^2$ is as defined herein before, with an acylating agent of the formula (IV) in the presence of a base and an optional activating agent,

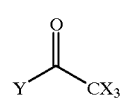

IV where X is a halogen independently selected from Cl, F or Br, and Y is a halogen or $OR^{12}$, where $R^{12}$ is $(C_1-C_6)$alkyl, $C(O)CX_3$, Het, or $(C_1-C_6)$alkyl(Het), where Het is pyridine or imidazole; and (ii) adding in situ a hydrazine compound of formula (V)

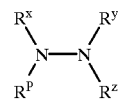

V where $R^P$ is H or $R^1$, where $R^1$ is as defined hereinbefore, and $R^x$, $R^y$ and $R^z$ are each independently selected from H, an electron donating group (EDG: e.g., trialkylsilyl), or an electron withdrawing group (EWG: e.g., tert-butyloxycarbonyl and trifluoroacetamide) wherein the electron withdrawing group or electron donating group is labile under the conditions of the reaction. The process of the present invention provides advantages over the multi-step processes for the preparation of compounds of general formula (II) as described in EP 812 845, EP 994 115, WO 98/49166 and WO 99/54333.

The compounds of formula (II) can be represented by the formulae (IIA) and (IIB) as detailed hereinafter.

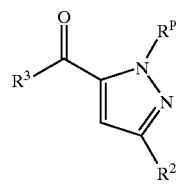

IIA

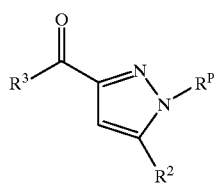

The process described above is referred to herein as "the process of the invention".

As used herein, the term "aryl" includes six- to ten-membered carbocyclic aromatic groups, such as phenyl and naphthyl and the like.

Het groups may be fully saturated, partly unsaturated, wholly aromatic, partly aromatic and/or bicyclic in character. Het groups that may be mentioned include groups such as optionally substituted azetidinyl, pyrrolidinyl, imidazolyl, indolyl, oxadiazolyl, thiadiazolyl, triazolyl, tetrazolyl, oxatriazolyl, thiatriazolyl, pyridazinyl, morpholinyl, pyrimidinyl, pyrazinyl, pyridyl, quinolinyl, isoquinolinyl, piperidinyl, pyrazolyl, imidazopyridinyl, piperazinyl, thienyl and furanyl.

The point of attachment of any Het group may be via any atom in the ring system including (where appropriate) a heteroatom. Het groups may also be present in the N- or S-oxidized form.

The term "$(C_1-C_6)$alkyl" (which includes the $(C_1-C_6)$ alkyl part of $(C_1-C_6)$alkylHet and $(C_1-C_6)$alkylaryl groups), when used herein, includes (e.g. methyl, ethyl, propyl, butyl, pentyl and hexyl groups). Unless otherwise specified, $(C_1-C_6)$alkyl groups may, when there is a sufficient number of carbon atoms, be linear or branched (e.g., iso-propyl, iso-butyl, sec-butyl, tert-butyl, isopentyl, neo-pentyl, tert-pentyl, 1-methylbutyl, 2-methylbutyl, 3-methylbutyl, hexyl, iso-hexyl, etc., including any stereoisomers thereof), or be saturated or unsaturated.

As defined herein, the term "halo" or "halogen", unless specified otherwise, includes fluoro, chloro, bromo and iodo.

Suitable bases for use herein preferably include tertiary amines, such as triethylamine and di-iso-propylethylamine, 1,5-diazabicyclo[4.3.0]non-5-ene, 1,8-diazabicyclo[5.4.0]undec-7-ene, 1,4-diazabicyclo[2.2.2]octane, imidazole; substituted pyridines, such as 4-(dimethylamino)pyridine; benzofused pyridines, such as quinoline and isoquinoline; hindered metal alkoxides; hindered metal aryloxides; metal carbonates and bicarbonates.

DETAILED DESCRIPTION

Advantageously, in the process according to the present invention, the direct addition of the hydrazine compound (V) to the reaction vessel containing the reaction mixture of (III), (IV) and base results in production of compounds (II) with desirable purity and yield. Scheme 1 below outlines the general procedures of the synthesis.

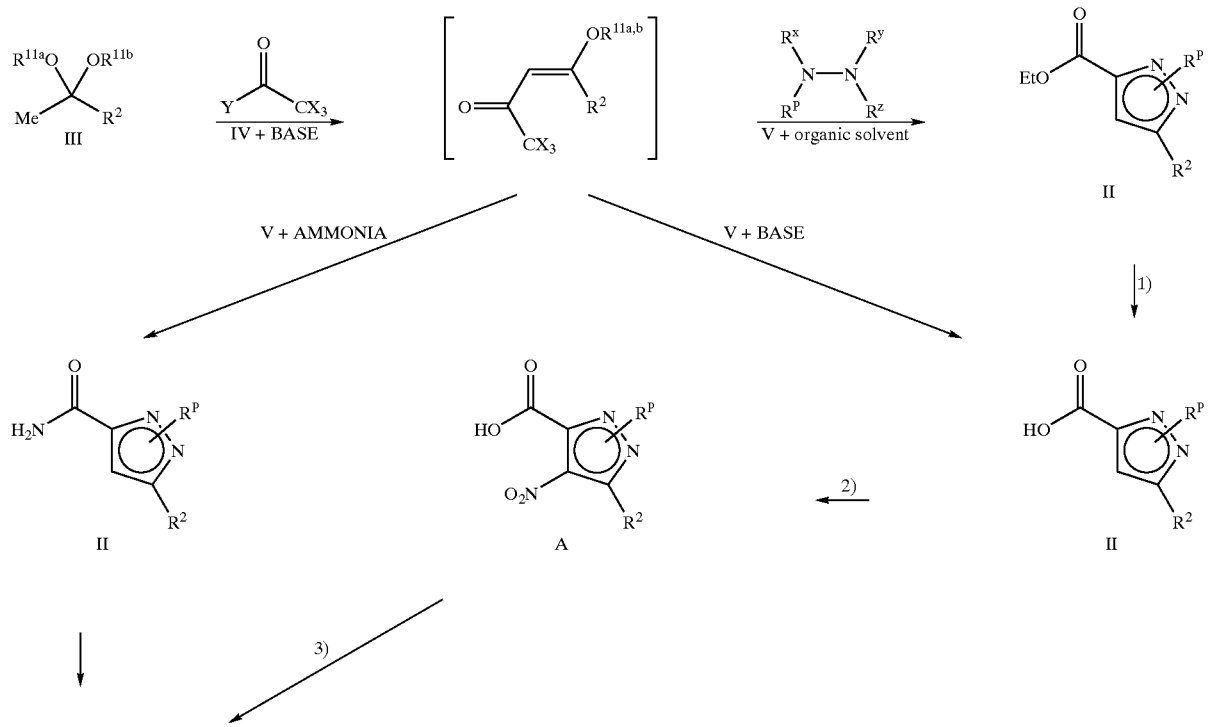

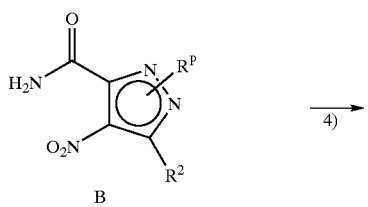

B

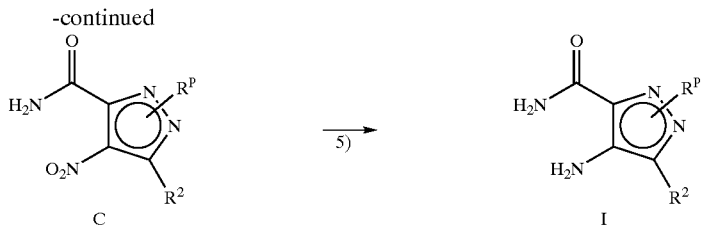

—continued

C →5) I

In a preferred aspect of the present invention there is provided a process for the production of pyrazole compounds of formula (II)

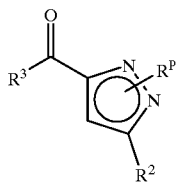

II wherein $R^P$ is H or $R^1$, where $R^1$ is $(C_1-C_4)$alkyl optionally substituted as hereinbefore described; $R^2$ is $(C_1-C_4)$alkyl; $R^3$ is $(C_1-C_3)$alkoxy, wherein the process comprises the step of (i) reacting a compound of formula (III),

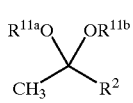

III wherein $R^{11a}$ and $R^{11b}$ are each independently $(C_1-C_4)$alkyl and $R^2$ is $(C_1-C_4)$alkyl, with an acylating agent of the formula (IV) in the presence of a base (preferably pyridine) and an optional activating agent

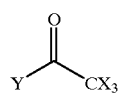

IV where X is Cl or F, and Y is Cl, F or $C(O)CX_3$; and (ii) adding to the same vessel a hydrazine compound of formula (V),

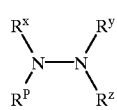

V wherein $R^P$ is H or $R^1$ where $R^1$ is as defined hereinbefore, and $R^x$, $R^y$, and $R^z$ are independently selected from H, an electron donating group, or an electron withdrawing group where the electron withdrawing group or the electron donating group is labile under the conditions of the reaction.

In a further preferred aspect of the present invention there is provided a process for the production of pyrazole compounds of formula (IIA),

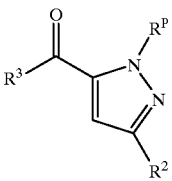

IIA wherein $R^P$ is H or $R^1$, where $R^1$ is $(C_1-C_4)$alkyl optionally substituted as hereinbefore described; $R^2$ is $(C_1-C_4)$alkyl; $R^3$ is $(C_1-C_3)$alkoxy, wherein the process comprises the steps of (i) reacting a compound of formula (III),

III where $R^{11a}$ and $R^{11b}$ are each independently $(C_1-C_4)$alkyl and $R^2$ is $(C_1-C_4)$alkyl, with an acylating agent of the formula (IV),

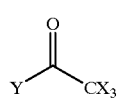

IV where X is Cl or F, and Y is Cl, F or $C(O)CX_3$, in the presence of a base (preferably pyridine) and an optional activating agent; and (ii) adding in situ a hydrazine compound of formula (V)

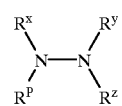

V where $R^P$ is H or $R^1$, where $R^1$ is as defined hereinbefore, and $R^x$=EWG, $R^y$ and $R^z$=H; or $R^x$ and $R^y$=H and $R^z$=EDG; or $R^x$=$R^y$=$R^z$=H when $R^1$=EWG; or $R^x$=EWG, $R^y$=H and $R^z$=EDG, wherein EWG is a tri$(C_1-C_2)$alkylsilyl group and EDG is tert-butyloxycarbonyl or trifluoroacetamide.

Scheme 2 illustrates the general procedures used in the synthesis of a compound of Formula (IIA).

Scheme 2

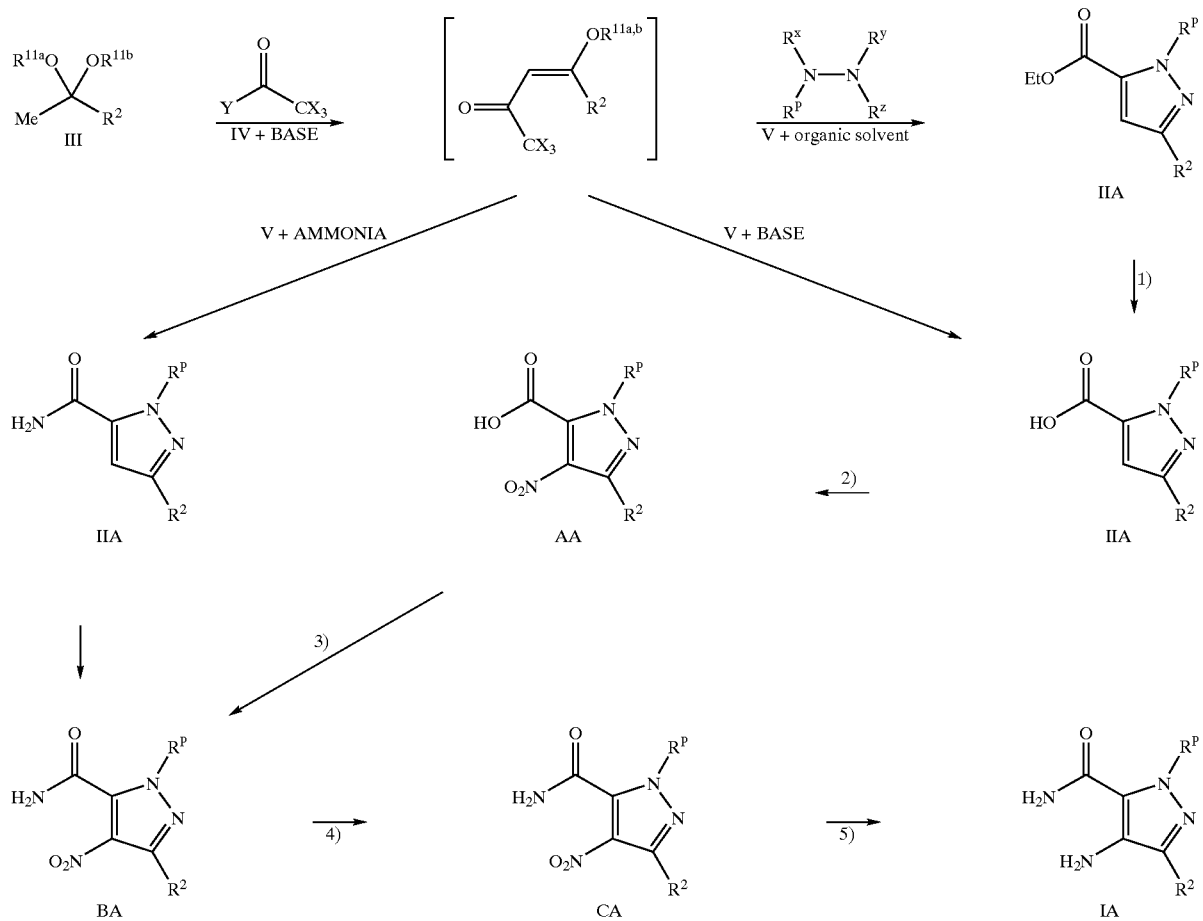

In yet another preferred aspect of the present invention there is provided a process for the production of pyrazole compounds of formula (IIB),

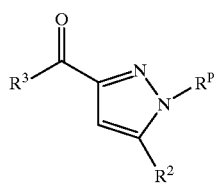
IIB wherein $R^P$ is H or $R^1$, where $R^1$ is $(C_1-C_4)$alkyl or $(C_1-C_4)$alkyl$((C_1-C_2)$ alkoxy); $R^2$ is $(C_1-C_4)$alkyl; and $R^3$ is $(C_1-C_3)$alkoxy, wherein the process comprises the steps of (i) reacting a compound of formula (III)

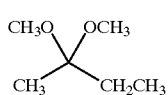
III with an acylating agent of formula (IV) in the presence of pyridine and an optional activating agent

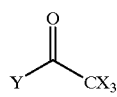
IV where X and Y are each independently Cl or F; and (ii) adding after about 8 hours to about 24 hours a hydrazine compound of formula (V)

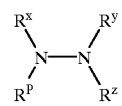
V wherein $R^P$ is H when
  $R^x$=EWG, $R^y$ and $R^z$=H; or
  $R^x$ and $R^y$=H and $R^z$=EDG; or
  $R^x$=$R^y$=$R^z$=H when $R^1$=EWG; or
  $R^x$=EWG, $R^y$=H and $R^z$=EDG, where EDG is a tri$(C_1-C_2)$alkylsilyl group and EWG is tert-butyloxycarbonyl or trifluoroacetamide;
and $R^P$ is $R^1$, where $R^1$ is as defined hereinbefore, when
  $R^x$=H, $R^y$=H and $R^z$=EWG; or
  $R^x$=EDG, $R^y$=H and $R^z$=H; or $R^x=R^y=R^z=H$ when $R^1$=EDG; or $R^x$=EDG, $R^y$=H and $R^z$=EWG, where EDG is a tri ($C_1$–$C_2$)alkylsilyl group and EWG is tert-butyloxycarbonyl or trifluoroacetamide.

Scheme 3 illustrates the general procedures used in the synthesis of a compound of Formula (IIB).

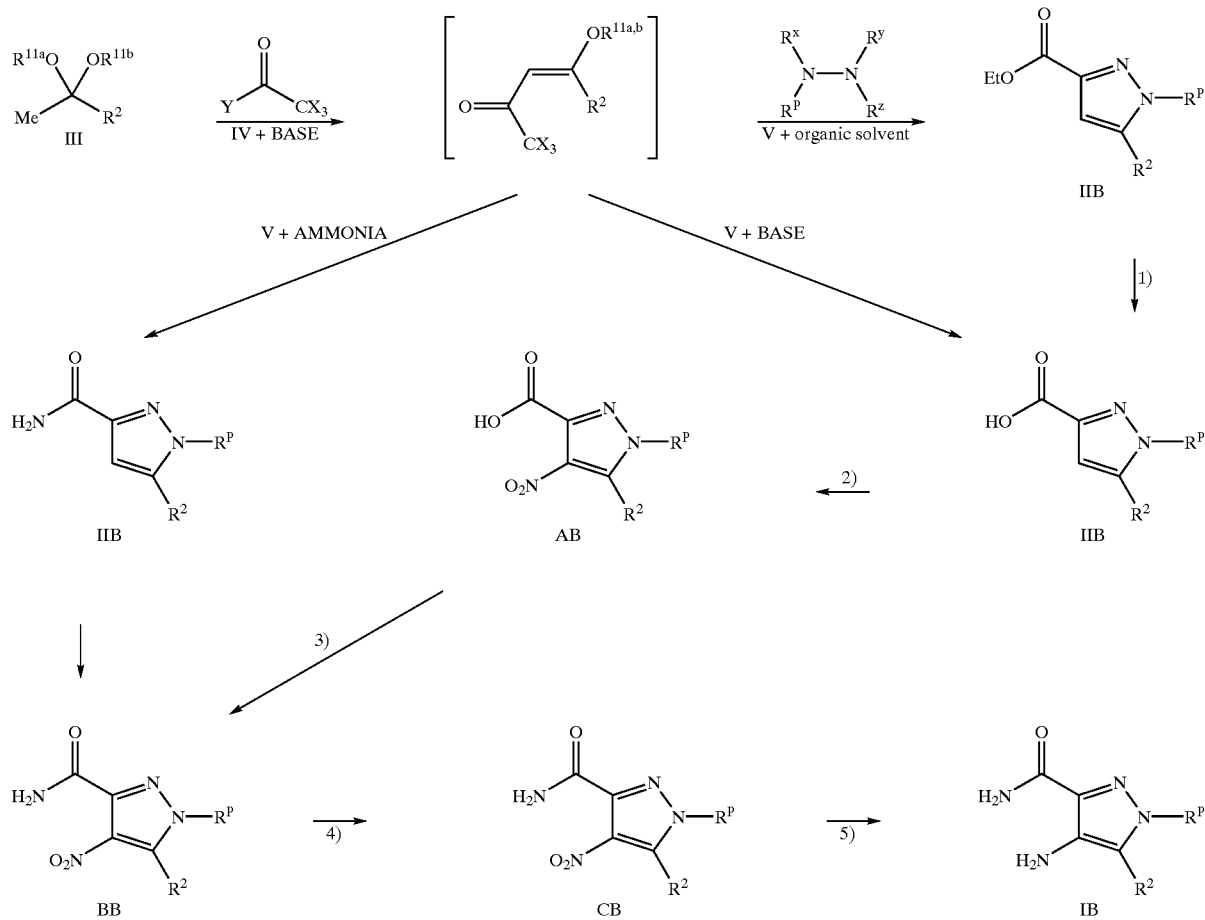

Scheme 3

The processes of the invention may be carried out in accordance with reaction conditions known to those skilled in the art.

The process according to the present invention may require an activating agent to "activate" the compound of formula (III) and at least one equivalent of an acylating agent of formula (IV) to "react" with the activated compound generated from the compound of formula (III). Any suitable agent capable of activating the compound of formula (III) may be used in conjunction with at least one equivalent of acylating agent of formula (IV) according to the process of the present invention.

Preferably, the activating agent is capable of converting an acetal to an enol ether under the basic reaction conditions. Suitable activating agents include trialkylsilyl halides, trialkylsilyl trifluoromethanesulfonates, oxalyl halides, 2-(trifluoroacetoxy)pyridine, 1-(trifluoroacetyl)imidazole, trifluoroacetyl chloride, trifluoroacetic anhydride, tribromoacetyl chloride and trichloroacetyl chloride. More preferred activators include 2-(trifluoroacetoxy)pyridine, 1-(trifluoroacetyl)imidazole, trifluoroacetyl chloride, trif-louroacetic anhydride, tribromoacetyl chloride and trichloroacetyl chloride.

In a preferred process of the present invention, the acylating agent of formula (IV) is used as both the activating agent and the acylating agent.

The acylating agent (IV) reacts with an enol ether to afford the key enone intermediate. Suitable reagents include be 2-(trifluoroacetoxy)-pyridine, 1-(trifluoroacetyl) imidazole, trifluoroacetyl chloride, trifluoroacetic anhydride, tribromoacetyl chloride and trichloroacetyl chloride. Preferred reagents include trifluoroacetic anhydride and trichloroacetyl chloride, even more preferred is trichloroacetylchloride.

Thus according to a yet further aspect of the present invention there is provided a process for the production of pyrazole compounds of formula (II), as defined hereinbefore, wherein the process comprises the steps of (i) reacting a compound of formula (III), as defined herein before, with at least one equivalent, more preferably at least two equivalents of an acylating agent of formula (IV), as defined hereinbefore, optionally in the presence of an activating agent, followed by the addition of a hydrazine compound of formula (V), as defined hereinbefore.

The reaction between the compound of the formula (III) and the activating agent (and/or the acylating agent of formula (IV), for reactions wherein the activating and acylating agents are the same) according to the process of the present invention may be carried out in an appropriate organic solvent system. The solvent system should not significantly react chemically with or significantly give rise to stereochemical changes in the reactants or product once formed, or significantly give rise to other side reactions. Suitable solvents include halogenated hydrocarbons (e.g., chloroform, dichloromethane and 1,2-dichloroethane), ethers (e.g., tetrahydrofuran, 1,4-dioxan, diethyl ether and tert-butyl methyl ether), aromatic hydrocarbons (e.g., toluene, xylenes and chlorobenzene) and alkyl acetates (e.g., ethyl acetate) and mixtures thereof. A preferred solvent is dichloromethane.

The reaction between the compound of formula (III) and the activating agent (and/or acylating agent of formula (IV)) according to the process of the present invention may be carried out at a temperature from about 0° C. to about room temperature, and, preferably, in an inert atmosphere (i.e. in the presence of an inert gas, such as nitrogen or argon).

Following the activation and acylation of the compound of formula (III), the hydrazine compound of formula (V) is added directly to the reaction mixture (of the activating agent (and/or acylating agent of formula (IV)) and the compound of formula (III)) in situ to provide a compound of formula (II) according to the process of the present invention. The hydrazine compound (V) may be added portionwise, dropwise, in solution or neat. Typically, the hydrazine compound is added in water and/or a suitable organic solvent (e.g. alcohols such as methanol, ethanol or iso-propanol) to provide a compound of formula (II) wherein $R^3$ is $(C_1-C_6)$alkoxy, or aqueous ammonia to provide a compound of formula (II) wherein $R^3$ is $NR^4R^5$ or mixtures thereof, followed by removal of the original reaction solvent (e.g. dichloromethane) and heat treatment.

In reactions with hydrazine compounds of formula (V) where $R^P = R^1$ and $R^1$ is an acid labile group such as a tert-butyloxycarbonyl group, the pH of the reaction mixture may be adjusted to between about pH 1.5 and about pH 3 and preferably to about pH 2 following addition of the hydrazine compound.

In reactions with hydrazine compounds of formula (V) where $R^P = H$, it is not necessary to adjust the pH of the reaction mixture following the addition of the hydrazine compound.

In a yet further aspect of the process of the present invention, compounds of formula (II) where $R^3 = OH$ may be prepared either via conversion of pyrazole compounds of formula (II) where $R^3 = $alkoxy as obtained according to the process described hereinbefore, or, alternatively via an in situ conversion (of the ester to the acid) where the pH of the reaction mixture is raised to greater than about pH 8 via addition of a suitable base (e.g, NaOH).

In yet another aspect of the process of the present invention, compounds of formula (II) prepared as outlined hereinbefore via (III), (IV) and (V) using aqueous ammonia as solvent (i.e. a compound of formula (II) where $R^3$ is $NR^4R^5$), may be converted directly to provide a compound of the formula B (as illustrated in Scheme 1 above).

Appropriate reaction times and reaction temperatures depend upon the solvent system that is employed, as well as the compound that is to be formed, but these may be determined routinely by the person skilled in the art.

Compounds of formula (III) when not commercially available may be prepared by known techniques as detailed in the preparations section herein.

Compounds of formulae (IV) and (V), and derivatives thereof, when not commercially available or not subsequently described, may be obtained by conventional synthetic procedures or by analogy with the processes described herein, in accordance with standard techniques, from readily available starting materials using appropriate reagents and reaction conditions.

According to a further aspect of the present invention, the compounds of formula (I):

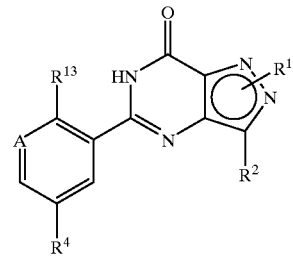

or a pharmaceutically or veterinarily acceptable salt thereof, or a pharmaceutically or veterinarily acceptable solvate of either entity, wherein A is CH or N;

$R^1$ is H, $(C_1-C_6)$alkyl, $(C_3-C_6)$alkenyl, $(C_3-C_6)$cycloalkyl, $(C_3-C_6)$cycloalkenyl, or $(C_1-C_3)$perfluoroalkyl, wherein the alkyl group may be branched or straight chain and wherein the alkyl, alkenyl, cycloalkyl or perfluoroalkyl group is optionally substituted by one or more substituents selected from hydroxy, $(C_1-C_4)$alkoxy, $(C_3-C_6)$cycloalkyl, $(C_1-C_3)$perfluoroalkyl, phenyl substituted with one or more substitutents selected from $(C_1-C_3)$alkyl, $(C_1-C_4)$alkoxy, $(C_1-C_4)$haloalky, or $(C_1-C_4)$haloalkoxy, wherein the haloalkyl and haloalkoxy groups contain one or more halo atoms, halo, CN, $NO_2$, $NHR^{11}$, $NHSO_2R^{12}$, $SO_2R^{12}$, $SO_2NHR^{11}$, $COR^{11}$, $CO_2R^{11}$ (where $R^{11}$ is H, $(C_1-C_4)$alkyl, $(C_2-C_4)$alkenyl, $(C_1-C_4)$alkanoyl, $(C_1-C_4)$haloalkyl, or $(C_1-C_4)$haloalkoxy and $R^{12}$ is $(C_1-C_4)$alkyl, $(C_2-C_4)$alkenyl, $(C_1-C_4)$alkanoyl, $(C_1-C_4)$haloalkyl, or $(C_1-C_4)$haloalkoxy), $NR^7R^8$, $CONR^7R^8$ or $NR^7COR^{11}$ (where $R^7$ and $R^8$ are each independently selected from H, $(C_1-C_4)$alkyl, $(C_2-C_4)$alkenyl, $(C_1-C_4)$alkoxy, $CO_2R^9$, $SO_2R^9$ wherein the alkyl, alkenyl or alkoxy groups are optionally substituted by $NR^5R^6$, $(C_1-C_4)$haloalkyl, or $(C_1-C_4)$haloalkoxy and $R^9$ is H, hydroxy$(C_2-C_3)$alkyl, $(C_1-C_4)$alkanoyl, or $(C_1-C_4)$alkyl optionally substituted with phenyl wherein the phenyl group is optionally substituted by one or more substituents selected from $(C_1-C_4)$alkyl (optionally substituted with $(C_1-C_4)$haloalkyl or $(C_1-C_4)$haloalkoxy, $(C_1-C_4)$alkoxy, halo, CN, $NO_2$, $NHR^{11}$, $NHSO_2R^{12}$, $SO_2R^{12}$, $SO_2NHR^{11}$, $COR^{11}$ or $CO_2R^{11}$), $Het^1$, $Het^2$, or $Het^3$; or $R^1$ is $Het^4$ or phenyl wherein the phenyl group is optionally substituted by one or more substituents selected from $(C_1-C_4)$alkyl, $(C_2-C_4)$alkenyl, $(C_1-C_4)$alkoxy, halo, CN, $CF_3$, $OCF_3$, $NO_2$, $NHR^{11}$, $NHSO_2R^{12}$, $SO_2R^{12}$, $SO_2NHR^{11}$, $COR^{11}$, or $CO_2R^{11}$;

$R^2$ is H, $(C_1-C_6)$alkyl, $(C_3-C_6)$alkenyl, or $(CH_2)_n$ $((C_3-C_6)$cycloalkyl$)$ where n is 0, 1, or 2 and the alkyl or alkyenyl group is optionally substituted with one or more fluoro substituents;

$R^{13}$ is $OR^3$ or $NR^5R^6$;

$R^3$ is $(C_1-C_6)$alkyl, $(C_3-C_6)$alkenyl, $(C_3-C_6)$alkynyl, $(C_3-C_7)$cycloalkyl, $(C_1-C_6)$perfluoroalkyl, or $((C_3-C_6)$cycloalkyl$)(C_1-C_6)$alkyl optionally substituted with one or two substituents selected from $(C_3-C_5)$cycloalkyl, hydroxy, $(C_1-C_4)$alkoxy, $(C_3-C_6)$alkenyl, $(C_3-C_6)$alkynyl, benzyloxy, NR⁵R⁶, phenyl, Het¹, Het², Het³, or Het⁴ wherein the (C₁–C₆)alkyl and (C₁–C₄)alkoxy groups may optionally be terminated by a haloalkyl group (e.g., CF₃), (C₃–C₆)cycloalkyl, Het¹, Het², Het³, or Het⁴;

R⁴ is (C₁–C₄)alkyl optionally substituted with OH, NR⁵R⁶, CN, CONR⁵R⁶ or CO₂R⁷, (C₂–C₄)alkenyl optionally substituted with CN, CONR⁵R⁶ or CO₂R⁷, (C₂–C₄) alkanoyl optionally substituted with NR⁵R⁶, hydroxy (C₂–C₄)alkyl optionally substituted with NR⁵R⁶, ((C₂–C₃) alkoxy)(C₁–C₂)alkyl optionally substituted with OH or NR⁵R⁶, CONR⁵R⁶, CO₂R⁷, halo, NR⁵R⁶, NHSO₂NR⁵R⁶, NHSO₂R⁸, phenyl optionally substituted with methyl, or heterocyclyl optionally substituted with methyl, or R⁴ is a pyrrolidinylsulphonyl, piperidinosulphonyl, morpholinosulphonyl, or piperazin-1-ylsulphonyl group having a substituent R¹⁰ at the 4-position of the piperazinyl group wherein the piperazinyl group is optionally substituted with one or two (C₁–C₄)alkyl, (C₁–C₃)alkoxy, NR⁷R⁸, or CON R⁷R⁸ groups and is optionally in the form of its 4-N-oxide;

R⁵ and R⁶ are each independently selected from H or (C₁–C₄)alkyl optionally substituted with (C₃–C₅)cycloalkyl, (C₁–C₄)alkoxy, or taken together with the nitrogen atom to which they are attached form an azetidinyl, pyrrolidinyl, piperidinyl, morpholinyl, 4-(NR⁹)- piperazinyl or imidazolyl group wherein the group is optionally substituted with methyl or hydroxy;

R¹⁰ is H, (C₁–C₆)alkyl, ((C₁–C₃)alkoxy)(C₂–C₆ )alkyl, hydroxy(C₂–C₆)alkyl, (R⁷R⁸N)(C₂–C₆)alkyl, (R⁷R⁸NCO) (C₁–C₆)alkyl, CONR⁷R⁸, CSNR⁷R⁸ or C(NH)NR⁷R⁸ optionally substituted with one or two substituents selected from hydroxy, NR⁵R⁶, CONR⁵R⁶, phenyl optionally substituted with (C₁–C₄)alkyl or (C₁–C₄)alkoxy, (C₂–C₆)alkenyl, or Het⁴;

Het¹ is an N-linked 4-, 5- or 6-membered nitrogen-containing heterocyclic group optionally containing one or more further heteroatoms selected from S, N or O;

Het² is a C-linked 5-membered heterocyclic group containing an O, S or N heteroatom optionally containing one or more heteroatoms selected from O or S;

Het³ is a C-linked 6-membered heterocyclic group containing an O or S heteroatom optionally containing one or more heteroatoms selected from O, S or N or Het³ is a C-linked 6-membered heterocyclic group containing three N heteroatoms;

Het⁴ is a C-linked 4-, 5- or 6-membered heterocyclic group containing one, two or three heteroatoms selected from S, O or N; and wherein any of the heterocyclic groups Het¹, Het², Het³ or Het⁴ may be saturated, partially unsaturated or aromatic and any of the heterocyclic groups may be optionally substituted with one or more substituents selected from (C₁–C₄)alkyl, (C₂–C₄)alkenyl, (C₁–C₄)alkoxy, halo, CO₂R¹¹, COR¹¹, SO₂R¹² or NHR¹¹ and/or any of the heterocyclic groups is benzo-fused;

or when R¹³ is OR or R³NR⁵, then

R¹ is Het, (C₁–C₆)alkylHet, aryl or (C₁–C₆)alkylaryl, which latter four groups are all optionally substituted with one or more substituents selected from halo, cyano, nitro, (C₁–C₆)alkyl, halo((C₁–C₆)alkyl), OR⁶, OC(O)R⁷, C(O)R⁸, C(O)OR⁹, C(O)NR¹⁰R¹¹, NR¹²R¹³ or SO₂NR¹⁴R¹⁵;

R² is H, halo, cyano, nitro, OR⁶, OC(O)R⁷, C(O)R⁸, C(O)OR⁹, C(O)NR¹⁰R¹¹, NR¹²R¹³, SO₂NR¹⁴R¹⁵, (C₁–C₆) alkyl, Het, (C₁–C₆)alkylHet, aryl or (C₁–C₆)alkylaryl, which latter five groups are all optionally substituted with one or more substituents selected from halo, cyano, nitro, (C₁–C₆)alkyl, halo((C₁–C₆)alkyl), OR⁶, OC(O)R⁷, C(O)R⁸, C(O)OR⁹, C(O)NR¹⁰R¹¹, NR¹²R¹³ or SO₂NR¹⁴R¹⁵;

R³ is H, (C₁–C₆)alkyl, (C₁–C₆)alkylHet, or (C₁–C₆) alkylaryl, which latter three groups are all optionally substituted with one or more substituents selected from halo, cyano, nitro, (C₁–C₆)alkyl, halo((C₁–C₆)alkyl), OR⁶, OC(O)R⁷, C(O)R⁸, C(O)OR⁹, C(O)NR¹⁰R¹¹, NR¹² R¹³ or SO₂NR¹⁴R¹⁵;

R⁴ is H, halo, cyano, nitro, halo((C₁–C₆)alkyl), OR⁶, OC(O)R⁷, C(O)R⁸, C(O)OR⁹, C(O)NR¹⁰R¹¹, NR¹²R¹³, NR¹⁶Y(O)R¹⁷, SOR¹⁸, SO₂R¹⁹R²⁰, C(O)AZ, (C₁–C₆)alkyl, (C₃–C₆)alkenyl, (C₃–C₆)alkynyl, Het, (C₁–C₆)alkylHet, aryl, (C₁–C₆)alkylaryl, which latter seven groups are all optionally substituted with one or more substituents selected from halo, cyano, nitro, (C₁–C₆)alkyl, halo((C₁–C₆)alkyl), OR⁶, OC(O)R⁷, C(O)R⁸, C(O)OR⁹, C(O)NR¹⁰R¹¹, NR¹²R¹³ or SO₂NR¹⁴R¹⁵;

Y is C or S(O), wherein one of R¹⁶ and R¹⁷ is not present when Y is S(O);

A is (C₁–C₆)alkylene;

Z is OR⁶, halo, Het or aryl, which latter two groups are both optionally substituted with one or more substituents selected from halo, cyano, nitro, (C₁–C₆)alkyl, halo((C₁–C₆) alkyl), OR⁶, OC(O)R⁷, C(O)R⁸, C(O)OR⁹, C(O)NR¹⁰R¹¹, NR¹²R¹³ or SO₂NR¹⁴R¹⁵;

R⁵, R⁶, R⁷, R⁸, R⁹, R¹⁸, R¹⁹ and R²⁰ are each independently H or (C₁–C₆)alkyl;

R¹⁰ and R¹¹ are each independently H, (C₁–C₆)alkyl optionally substituted with one or more substituents selected from halo, cyano, nitro, (C₁–C₆)alkyl, halo((C₁–C₆)alkyl), OR⁶, OC(O)R⁷, C(O)R , C(O)OR⁹, C(O)NR¹⁰R¹¹, NR¹²R¹³, or SO₂NR¹⁴R¹⁵, Het or aryl optionally substituted with one or more substituents selected from halo, cyano, nitro, (C₁–C₆)alkyl, halo((C₁–C₆)alkyl), OR⁶, OC(O)R⁷, C(O)R⁸, C(O)OR⁹, C(O)NR¹⁰R¹¹, NR¹²R¹³, or SO₂NR¹⁴R¹⁵, or one of R¹⁰ and R¹¹ may be (C₁–C₆)alkoxy, amino, or Het, which latter two groups are both optionally substituted with (C₁–C₆)alkyl;

R¹² and R¹³ are each independently H or (C₁–C₆)alkyl, or one of R¹² or R¹³ may be C(O)-(C₁–C₆)alkyl or C(O)Het in which Het is optionally substituted with (C₁–C₆)alkyl;

R¹⁴ and R¹⁵ are each independently H or (C₁–C₆)alkyl, or R¹⁴ and R¹⁵ taken together with the nitrogen atom to which they are bound form a heterocyclic ring;

R¹⁶ and R¹⁷ are each independently H or (C₁–C₆)alkyl, or one of R¹⁶ and R¹⁷ may be Het or aryl, which latter two groups are both optionally substituted with (C₁–C₆)alkyl;

Het is an optionally substituted four to twelve membered heterocyclic group, which may be aromatic or non-aromatic, contain one or more double bonds, mono- or bi-cyclic and contains one or more heteroatoms selected from the group consisting of N, S and O;

wherein the compounds may be prepared from compounds of formula (VIII)

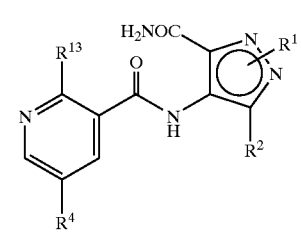

(VII)

wherein R¹, R², R⁴ and R¹³ are as defined hereinbefore and the compound of formula (VIII) is prepared from the reaction of a compound of formula (VII),

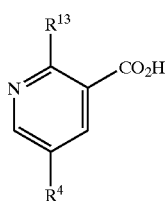
(VII)

where $R^4$ and $R^{13}$ are as defined herein before, via coupling with a compound of formula (VI),

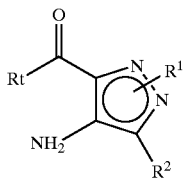
VI where $R^1$ and $R^2$ are as defined hereinbefore and $R^1$ is $NR^pR^q$, where $R^p$ and $R^q$ are each independently H or $(C_1-C_6)$alkyl, and the compound of formula (VI) is prepared by nitration and hydrogenation of a compound of formula (II),

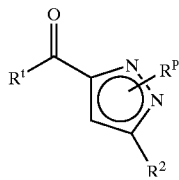
II where $R^t$ and $R^2$ are as defined hereinbefore and $R^P$ is $R^1$ as defined hereinbefore, wherein the compound of formula (II) is prepared by reacting in the presence of a base and an optional activating agent a compound of formula (III),

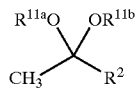
III where $R^{11a}$ and $R^{11b}$ are each independently $(C_1-C_6)$alkyl and $R^2$ is as defined herein before, with an acylating agent of formula (IV),

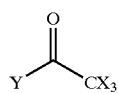
IV where X is halogen independently selected from Cl, F or Br, and Y is halogen or $OR^{12}$ where $R^{12}$ is $(C_1-C_6)$alkyl, $C(O)CX_3$, Het, or $(C_1-C_6)$alkyl(Het) where Het is pyridine or imidazole; and then adding in situ a hydrazine compound of formula (V),

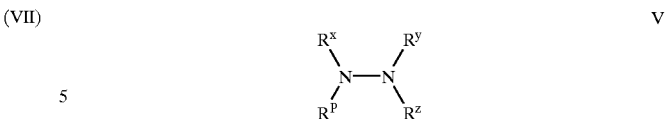
V where $R^P$ is H or $R^1$ where $R^1$ is as defined hereinbefore, and $R^x$, $R^y$ and $R^z$ are each independently selected from H, an electron donating group (EDG), or an electron withdrawing group (EWG) where the electron withdrawing group or the electron donating group is labile under the conditions of the reaction.

According to a preferred process of the present invention, compounds of formula (I) are prepared from compounds of formula (II) wherein $R^1$ is H, $(C_1-C_6)$alkyl, $(C_1-C_6)$alkoxy, $(C_3-C_6)$cycloalkyl, $(C_1-C_6)$alkyl($(C_1-C_6)$alkoxy), Het, $(C_1-C_6)$alkylHet, aryl or $(C_1-C_6)$alkylaryl, which latter eight groups are all optionally substituted by one or more substituents selected from the group consisting of halo, cyano, nitro, $(C_1-C_6)$alkyl, $C(O)NR^4R^5$, $C(O)R^6$, $C(O)OR^7$, $OR^8$, $NR^{9a}R^{9b}$ and $SO_2NR^{10a}R^{10b}$;

$R^2$ is $(C_1-C_6)$alkyl, $(C_1-C_6)$alkoxy, $(C_3-C_6)$cycloalkyl, $(C_1-C_6)$alkyl($(C_1-C_6)$alkoxy), Het, $(C_1-C_6)$alkylHet, aryl, or $(C_1-C_6)$alkylaryl, which latter eight groups are all optionally substituted by one or more substituents selected from the group consisting of halo, cyano, nitro, $(C_1-C_6)$alkyl, $C(O)NR^4R^5$, $C(O)R^6$, $C(O)OR^7$, $OR^8$, $NR^{9a}R^{9b}$ and $SO_2NR^{10a}R^{10b}$;

$R^t$ is $NR^PR^q$;

$R^P$, $R^q$, $R^6$, $R^7$, $R^8$, $R^{10a}$ and $R^{10b}$ are each independently H or $(C_1-C_6)$alkyl;

$R^{9a}$ and $R^{9b}$ are each independently H, $(C_1-C_6)$alkyl or taken together with the nitrogen atom to which they are attached form an azetidinyl, pyrollidinyl or piperidinyl group;

$R^4$ is $CO_2R^7$, $(C_1-C_4)$alkyl optionally substituted with OH, $NR^5R^6$, CN, $CONR^5R^6$ or $CO_2R^7$, or $R^4$ is a pyrrolidinylsulphonyl, piperidinosulphonyl, morpholinosulphonyl, or piperazin-1-ylsulphonyl group having a substituent, $R^{10}$ at the 4-position of the piperazinyl group wherein the piperazinyl group is optionally substituted with one or two $(C_1-C_4)$alkyl, $(C_1-C_3)$alkoxy, $NR^7R^8$ or CON $R^7R^8$ groups and is optionally in the form of its 4-N-oxide; and $R^{10}$ is H or $(C_1-C_6)$alkyl.

A highly preferred process for the preparation of compounds of formula (I) from compounds of formula (II) is when $R^1$ is $(C_1-C_4)$alkyl, where alkyl group is optionally interrupted by an oxygen atom and/or is optionally terminated by a Het group (such as a pyridinyl group);

$R^2$ is $(C_1-C_4)$alkyl;

$R^3$ is $(C_1-C_5)$alkyl optionally interrupted by an oxygen atom;

$R^4$ is $CO_2R^7$, or a morpholinosulphonyl or piperazin-1-ylsulphonyl group having a substituent $R^{10}$ at the 4-position of the piperazinyl group where $R^{10}$ is H, methyl, or ethyl.

More preferred compounds of formulae 1, IA and IB prepared according to a process of the present invention include those in which $R^1$ is a linear $(C_1-C_3)$alkyl optionally interrupted by an oxygen atom, or is optionally terminated by a 2-pyridinyl group (e.g. to form a 2-pyridinylmethyl group);

$R^2$ is a linear $(C_2-C_3)$alkyl;

$R^3$ is a linear or branched $(C_2-C_4)$alkyl optionally interrupted by an oxygen atom;

$R^4$ is $CO_2R^7$, or a morpholinosulphonyl or piperazin-1-ylsulphonyl group having a substituent $R^{10}$ at the 4-position of the piperazinyl group where $R^{10}$ is methyl or ethyl.

Particularly preferred compounds that may be formed according to a process of the present invention include sildenafil (1A), and the following five compounds:

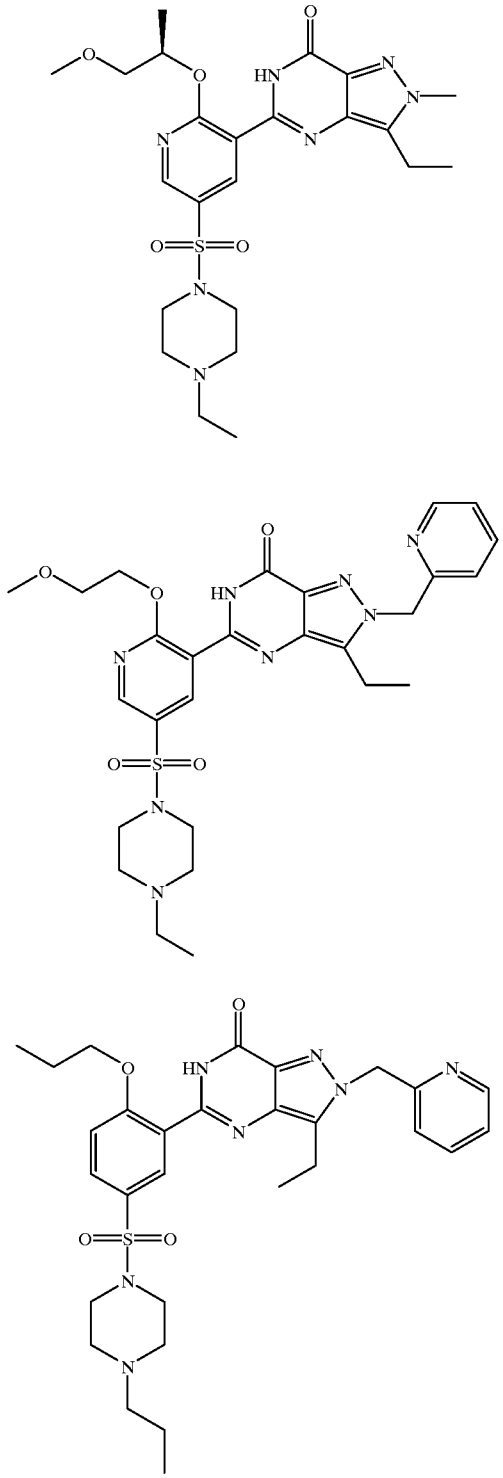

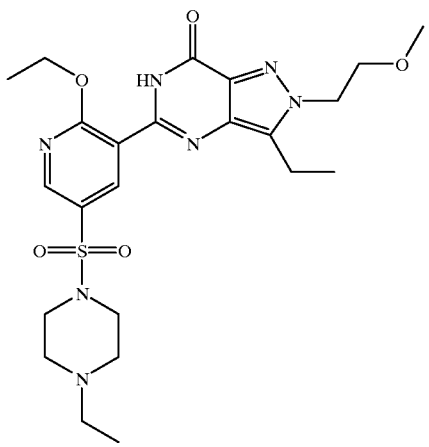

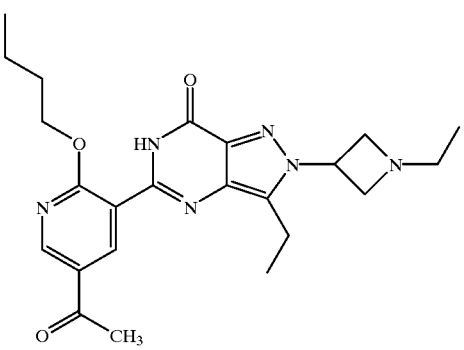

Compound 1B is also known as (+)-3-ethyl-5-[5-(4-ethylpiperazin-1 -ylsulphonyl)-2-(2-methoxy-1(R)-methylethoxy)pyridin-3-yl]-2-methyl-2,6-dihydro-7H-pyrazolo[4,3-d]pyrimidin-7-one, or alternatively as 3-ethyl-5-{5-[4-ethylpiperazin-1-ylsulphonyl]-2-([(1R)-2-methoxy-1-methylethyl]oxy)pyridin-3-yl)-}2-methyl-2,6-dihydro-7H-pyrazolo[4,3-d]pyrimidin-7-one (the compound of Example 118 of WO99/54333).

Compound 1C is also known as 3-ethyl-5-[5-(4-ethylpiperazin-1-ylsulphonyl)-2-n-propoxyphenyl]-2-(pyridin-2-yl)-methyl-2,6-dihydro-7H-pyrazolo[4,3-d] pyrimidin-7-one (the compound of Example 5 of WO98/49166).

Compound 1D is also known as 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo[4,3-d]pyrimidin-7-one (the compound of Example 4 of WO99/54333).

Compound 1E is also known as 5-[2-Ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, or alternatively as 1-{6-ethoxy-5-[3-ethyl-6,7-dihydro-2-(2-methoxyethyl)-7-oxo-2H-pyrazolo[4,3-d] pyrimidin-5-yl]-3-pyridyl sulphonyl}-4-ethylpiperazine (the compound of Example 103 of WO 01/27113 and exemplified hereinafter as Example 1).

Compound 1F is also known as 5-(5-acetyl-2-butoxy-3-pyridinyl)-3-ethyl-2-(1-ethyl-2-(1-ethyl-3-azetidinyl)-2,6-dihydro-7H-pyrazolo[4,3-d]pyrimidin-7-one (the compound of Example 132 of WO 01/27112 and exemplified hereinafter as Example 2).

Compounds of formulae (II) may contain one or more asymmetric carbon atoms and may therefore exhibit optical and/or diastereoisomerism. The process of the invention thus also relates to the formation of stereoisomers of compounds of formulae II and mixtures thereof. Stereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively, the desired optical isomers may be made by reaction of the appropriate optically active starting materials under conditions that will not cause racemization or epimerization, or by derivatization, for example with a homochiral acid followed by separation of the diastereomeric esters by conventional means (e.g. HPLC, crystallisation, chromatography over silica or, for example, via classical resolution with a homochiral acid salt). The formation of all stereoisomers is included within the scope of the invention.

Compounds may be isolated from reaction mixtures using known techniques.

Substituents on the aryl (e.g. phenyl), and (if appropriate) heterocyclic, group(s) in compounds defined herein may be converted to other substituents using techniques well known to those skilled in the art. For example, amino may be converted to amido, amido may be hydrolysed to amino, hydroxy may be converted to alkoxy, alkoxy may be hydrolyzed to hydroxy etc.

It will be appreciated by those skilled in the art that in the processes described above the functional groups of intermediate compounds may be or may need to be protected by protecting groups.

Functional groups that may be desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl, benzyl and alkylcarbonyl groups (e.g. methyl- and ethylcarbonyl groups). Suitable protecting groups for amino include benzyl, tert-butyloxycarbonyl, 9-fluorenylmethoxycarbonyl or benzyloxycarbonyl. Suitable protecting groups for carboxylic acid include ($C_1$–$C_6$)alkyl, allyl or benzyl esters.

The protection and deprotection of functional groups may take place before or after any of the reaction steps described hereinbefore.

Protecting groups may be removed in accordance with techniques which are well known to those skilled in the art and as described hereinafter.

The use of protecting groups is fully described in "Protective Groups in Organic Chemistry", edited by J W F McOmie, Plenum Press (1973), and "Protective Groups in Organic Synthesis", $3^{rd}$ edition, T W Greene & P G M Wutz, Wiley-Interscience (1999).

The process of the invention possesses the advantage that the intermediate pyrazoles of formula (II) that are used in the synthesis of pyrimidin-7-ones, and in particular in the preparation of sildenafil (compound (IA) herein) may be prepared from commercially-available starting materials in fewer steps than in processes described in the prior art without concomitant losses in yield of key intermediates and of final compounds. Further, the pyrazoles are obtained in desirable levels of purity according to the process of the present invention.

Further, the process of the invention may have the advantage that pyrazole compounds of formula (II) may be prepared in less time, more conveniently, and at a lower cost than when prepared in processes described in the prior art.

The invention is illustrated, but in no way limited, by the following examples.

EXAMPLES

All $^1$H NMR spectra were recorded using a Varian Unity 300 MHz machine.

Preparation 1

2,2-dimethoxybutane:

Methyl ethyl ketone (672 mL) was charged to a 2 L round bottomed flask and stirred at room temperature before being treated with, trimethylorthoformate (763 mL) and para-toluenesulphonic acid (6.65 g, 0.5 mol %). Over a 15 min period the internal temperature rose to 46° C., so the reaction was cooled to 0° C. for 30 min. The reaction was then stirred at room temperature for 2 h. The reaction was then neutralised by pouring onto sodium carbonate (ca. 750 g) with constant stirring. The resultant slurry was filtered under vacuum and the resultant filtrate was distilled at atmospheric pressure. The fraction boiling in the range 118° C.–124° C. was collected as a colourless liquid, 582 g, 70%.

$^1$H NMR (CDCl$_3$): δ=0.88 (3H, t), 1.24 (3H, s), 1.61 (2H, q), 3.17 (6H, s).

Example 1

N-[3-Carbamoyl-5-ethyl-1-(2-methoxyethyl)-1H-pyrazol-4-yl]-2-ethoxy-5-(4-ethyl-1-piperazinyl sulfonyl) nicotinamide (a) Ethyl 3-ethyl-1H-pyrazole-5-carboxylate (IIA) from (III) and (V)

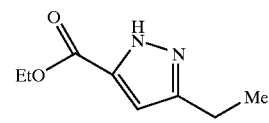

To a stirred solution of 2,2-dimethoxybutane (10 g, 84.7 mMol) in CH$_2$Cl$_2$ (50 mL) under a nitrogen atmosphere at 0° C. was added pyridine (13.7 mL, 169.5 mMol). The reaction mixture was maintained at 0° C. and a solution of trichloroacetyl chloride (18.9 mL, 169.5 mMol) in CH$_2$Cl$_2$ (35 mL) was added over 1 hour with constant stirring. The yellow-orange solution begins to precipitate a white solid as the reaction progresses. The reaction mixture is allowed to warm to room temperature over 20 h. The reaction mixture was diluted with ethanol (150 mL) and re-cooled to 0° C. before treatment with hydrazine hydrate (8.2 mL, 169.5 mMol) as a solution in ethanol (35 mL) over 30 min. The reaction was heated to 50° C. and solvent was distilled at atmospheric pressure. The temperature was increased until the head temperature reached 78° C. Reflux was maintained for a further 2 h, before cooling to room temperature. The reaction mixture was diluted with water (250 mL) and ethanol was removed by evaporation at reduced pressure. The resultant mixture was extracted with CH$_2$Cl$_2$ (3×200 mL). The combined organics were dried (MgSO$_4$), filtered and evaporated at reduced pressure to afford the title compound as a brown oil, 12.05 g, 85%.

$^1$H NMR (300 MHz, CDCl$_3$): δ=1.20 (3H, t), 1.28 (3H, t), 2.67 (2H, q), 4.29 (2H, q), 6.55 (1H, s), 12.56 (1H, s).

LRMS m/z=167.1 [M-H]$^+$, C$_8$H$_{12}$N$_2$O$_2$ requires 168.2.

(b) Ethyl 3-ethyl-1H-pyrazole-5-carboxylic acid (IIA) from (IIA) via route 1

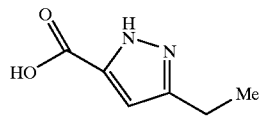

Aqueous sodium hydroxide solution (10M; 100 ml, 1.0 mol) was added dropwise to a stirred suspension of the title compound of Example (a) (66.0 g, 0.39 mol) in methanol and the resulting solution heated under reflux for 4 hours. The cool reaction mixture was concentrated under reduced pressure to ca. 200 ml, diluted with water (200 ml) and this mixture washed with toluene (3×100 ml). The resulting aqueous phase was acidified with concentrated hydrochloric acid to pH 4 and the white precipitate collected and dried by suction to provide the title compound (34.1 g). δ (DMSO$_{d6}$): 1.13 (3H,t), 2.56 (2H,q), 6.42 (1H,s).

(c) 4-Nitro-3-n-propyl-1H-pyrazole-5-carboxylic acid

Fuming sulphuric acid (17.8 ml) was added dropwise to stirred, ice-cooled fuming nitric acid (16.0 ml), the resulting solution heated to 50° C., then 3-n-propyl-1H-pyrazole-5-carboxylic acid (*Chem. Pharm. Bull.,* 1984, 32,1568; 16.4 g, 0.106 mol) added portionwise over 30 minutes whilst maintaining the reaction temperature below 60° C. The resulting solution was heated for 18 hours at 60° C., allowed to cool, then poured onto ice. The white precipitate was collected, washed with water and dried by suction to yield the title compound (15.4 g), m.p. 170–172° C. Found: C, 42.35; H, 4.56; N, 21.07. C$_7$H$_9$N$_3$O$_4$ requires C, 42.21; H, 4.55; N, 21.10%. δ (DMSO$_{d6}$): 0.90 (3H,t), 1.64 (2H,m), 2.83 (2H, m), 14.00 (1 H,s).

(d) 3-Ethyl-4-nitro-1H-pyrazole-5-carboxylic acid (IIA) to (AA) via route 2

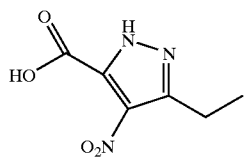

Obtained from the title compound of Example (b), by analogy with the process of Example (c), as a brown solid (64%). δ (DMSO$_{d6}$): 1.18 (3H,t), 2.84 (2H,m), 13.72 (1 H,s).

(e) 4-Nitro-3-n-propyl-1H-pyrazole-5-carboxamide

A solution of the title compound of Example (c) (15.4 g, 0.077 mol) in thionyl chloride (75 ml) was heated under reflux for 3 hours and then the cool reaction mixture evaporated under reduced pressure. The residue was azeotroped with tetrahydrofuran (2×50 ml) and subsequently suspended in tetrahydrofuran (50 ml), then the stirred suspension ice-cooled and treated with gaseous ammonia for 1 hour. Water (50 ml) was added and the resulting mixture evaporated under reduced pressure to give a solid which, after trituration with water and drying by suction, furnished the title compound (14.3 g).

m.p. 197–199° C. Found: C, 42.35; H, 5.07; N, 28.38. C$_7$H$_{10}$N$_4$O$_3$ requires C, 42.42; H, 5.09; N, 28.27%. δ (DMSOd$_6$): 0.90 (3H,t), 1.68 (2H,m), 2.86 (2H,t), 7.68 (1 H,s), 8.00 (1 H,s).

(f) 3-Ethyl-4-nitro-1H-pyrazole-5-carboxamide BA from AA via route 3

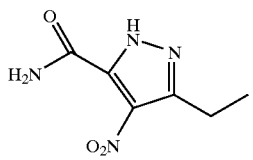

Obtained from the title compound of Example (d), by analogy with Example (e), as a white solid (90%). δ (DMSO$_{d6}$): 1.17 (3H,t), 2.87 (2H,m), 7.40 (1H,s), 7.60 (1H,s), 7.90 (1H,s). LRMS: m/z 185 (M+l)$^+$.

(g)(i) 5-Ethyl-1-(2-methoxyethyl)-4-nitro-1H-pyrazole-3-carboxamide CA from BA via route 4

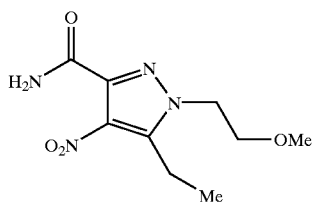

A mixture of 3-ethyl-4-nitro-1H-pyrazole-5-carboxamide (2.5 kg, 13.6 Mol), sodium carbonate (1.8 Kg, 17.0 Mol) and 2-bromoethyl methyl ether (1.98 kg, 14.2 Mol) in THF (22.5 L) and water (2.5 L) was heated under reflux and stirred for 20 hours. The mixture was cooled to ambient temperature and CH$_2$Cl$_2$ (67.5 L) and water (22.5 L) were added. The resultant organic and aqueous layers were separated. The aqueous phase was extracted with CH$_2$Cl$_2$ (22.5 L) and the combined organic solution was distilled under atmospheric pressure and replaced with ethyl acetate (33 L) to a final volume of 17 L. The cooled mixture was granulated at ambient temperature for 2 hours, filtered and washed with ethyl acetate (2.5 L). This afforded 5-ethyl-1-(2-methoxyethyl)-4-nitro-1H-pyrazole-3-carboxamide as a white crystalline solid, 2.10 kg, 57%. m.p.=140° C. Found: C, 44.46; H, 5.79; N, 23.01. C$_9$H$_{14}$N$_4$O$_4$ requires C, 44.63; H, 5.79; N, 23.14%.

δ (CDCl$_3$): 1.18 (3H, t), 2.98 (2H, q), 3.22 (3H, s), 3.77 (2H, t), 4.28 (2H, q), 6.03 (1H, s), 7.36 (1H, s).

LRMS: m/z=243 (M+1)$^+$ (g)(ii) 5-Ethyl-1-(2-methoxyethyl)-4-nitro-1H-pyrazole-3-carboxamide.

A mixture of 3-ethyl-4-nitro-1H-pyrazole-5-carboxamide (25 g, 0.136 Mol), sodium carbonate (18 g, 0.17 Mol) and sodium iodide (20.4 g, 0.136 Mol) were suspended in ethyl methyl ketone (125 mL) at room temperature. 2-bromoethyl methyl ether (12.8 mL, 0.142 Mol) was added and the mixture was heated to reflux and stirred for 70 hours. The mixture was cooled to ambient temperature and water (250 mL) was added. The resultant slurry was warmed to reflux and held at that temperature for 30 min before cooling to room temperature. The resultant precipitate was granulated at room temperature for 3 h, filtered and vacuum dried to afford 5-ethyl-1-(2-methoxyethyl)-4-nitro-1H-pyrazole-3-carboxamide as a yellow crystalline solid 24.3 g, 74%. Data as reported for Example (g)(i).

(h) 4-Amino-5-ethyl-1-(2-methoxyethyl)-1H-pyrazole-3-carboxamide (IA) from CA via route 5

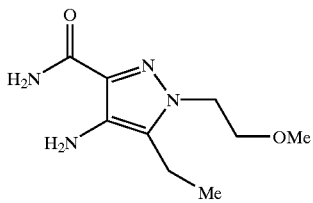

A mixture of 5-ethyl-1-(2-methoxyethyl)-4-nitro-1H-pyrazole-3-carboxamide (20 g, 82.6 mMol) and 5% Pd/C (1 g) in methanol (200 mL) was pressurised at 50psi/25° C. in a sealed vessel and stirred for 15 hours. At the end of the reaction the mixture was filtered through arbocel and the filter cake was washed with methanol. The methanolic solution was distilled at atmospheric pressure and replaced with ethyl acetate to a final volume of 100 mL. The cooled mixture was granulated at ambient temperature for 2 h filtered and washed with ethyl acetate (20 mL) to afford 4-amino-5-ethyl-1-(2-methoxyethyl)-1H-pyrazole-3-carboxamide as a white crystalline solid, 15 g, 88%. m.p.= 131° C. Found: C, 50.75; H, 7.62; N, 26.38. $C_9H_{16}N_4O_2$ requires C, 50.94; H, 7.55; N, 26.42%. δ (CDCl$_3$): 1.20 (3H, t), 2.63 (2H, q), 3.32 (3H, s), 3.74 (2H, t), 3.95 (2H, s), 4.15 (2H, t), 5.27 (1H, s), 6.59 (1H, s).

LRMS: m/z=213 (M+1)$^+$ (i) N-[3-Carbamoyl-5-ethyl-1-(2-methoxyethyl)-1H-pyrazol-4-yl]-2-ethoxy-5-(4-ethyl-1-piperazinyl sulfonyl) nicotinamide.

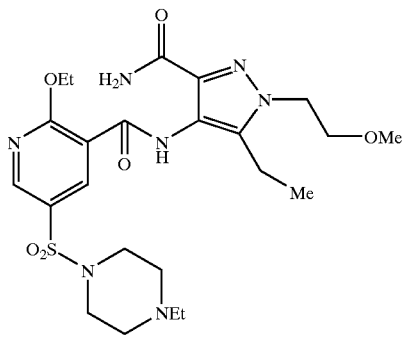

2-ethoxy-5-(4-ethyl-1-piperazinylsulfonyl)nicotinic acid (2.31 kg, 6.73 Mol) was suspended in ethyl acetate (16.2 L) and 1,1-carbonyldimidazole (1.09 kg, 6.73 Mol) was added at room temperature. The reaction mixture was heated at 45° C. for 40 minutes and then the reaction was stirred for a further 40 minutes at reflux. After cooling to ambient temperature 4-amino-5-ethyl-1-(2-methoxyethyl)-1H-pyrazole-3-carboxamide (1.5 kg, 7.06 Mol) was added to the cooled mixture, and the reaction stirred for a further 15 hours under reflux. The mixture was cooled filtered and the filter cake was washed with 90% water/10% ethyl acetate, (2 mL /g) to afford N-[3-carbamoyl-5-ethyl-1-(2-methoxyethyl)-1H-pyrazol-4-yl}-2-ethoxy-5-(4-ethyl-1-piperazinyl sulfonyl) nicotinamide as an off white crystalline solid, 3.16 kg, 88%. m.p.=156° C. Found: C, 51.33; H, 6.56; N, 18.36. $C_{23}H_{35}N_7O_6S$ requires C, 51.40; H, 6.53; N, 18.25%.

δ (CDCl$_3$): 1.04 (3H, t), 1.22 (3H, t), 1.60 (3H, t), 2.44 (2H, q), 2.54 (4H, m), 2.96 (2H, q), 3.12 (4H, m), 3.36 (3H, s), 3.81 (2H, t), 4.27 (2H, t), 4.80(2H, q), 5.35(1H, s), 6.68 (1H, s), 8.66 (1H, d), 8.86 (1H, d), 10.51 (1H, s).

LRMS: m/z=539 (M+1)$^+$ (i) 1-(6-Ethoxy-5-[3-ethyl1-6,7-dihydro-2-(2-methoxyethyl)-7-oxo-2H-pyrazole[4,3-d]pyrimidin-5-yl]-3-pyridylsulfonyl)-4-ethylpiperazine•ethyl acetate solvate.

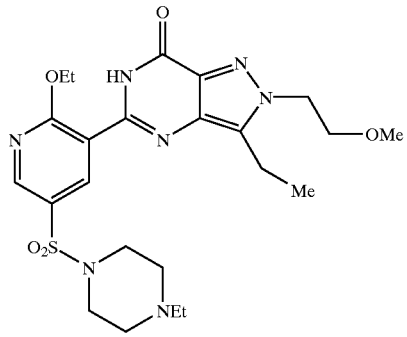

A mixture of N-[3-carbamoyl-5-ethyl-1-(2-methoxyethyl)-1H-pyrazol-4-yl}-2-ethoxy-5-(4-ethyl-1-piperazinyl sulfonyl) nicotinamide (1.18 kg, 2.2 Mol), potassium tert-butoxide (500 g, 4.4 moles) and ethyl acetate (193 g) in ethanol (11.8 L) was heated at 120° C. for 20 hours. The reaction mixture was then concentrated under reduced pressure, in total approx. 10 L of solvent were distilled. To the residue water (2.9 L) was added and the mixture stirred at room temperature while aqueous HCl was added until pH 7.5 was obtained. Ethyl acetate (7.5 L) was added and the two phase mixture was warmed to 55° C. The organic phase was separated and the aqueous phase was extracted with further ethyl acetate (3.0 L). The combined organic phases were distilled at atmospheric pressure to a final volume of 4 L. The precipitated solids were granulated at 5° C. for 1 h, filtered and washed with ethyl acetate (1.2 L) and dried under vacuum. This afforded 1-(6-Ethoxy-5-[3-ethyl]-6,7-dihydro-2-(2-methoxyethyl)-7-oxo-2H-pyrazole[4,3-d]pyrimidin-5-yl]-3-pyridylsulfonyl)-4-ethylpiperazine as a light yellow crystalline solid, 877 g, 78%. m.p.=157° C. Found: C, 52.65; H, 6.46; N, 17.76. $C_{23}H_{33}N_7O_5S$. 0.2 $C_2H_5CO_2CH_3$ requires C, 53.21; H, 6.49; N, 18.25%.

δ (CDCl$_3$): 1.07 (3H, t), 1.42 (3H, t), 1.61 (3H, t), 2.44 (2H, q), 2.57 (4H, m), 3.08 (2H, q), 3.15 (4H, m), 3.32 (3H, s), 3.92 (2H, q), 4.48 (2H, q), 4.77 (2H, q), 8.65 (1H, d), 9.06 (1H, d). The spectrum also has signals that correspond to a solvate with ethyl acetate.

LRMS: m/z=520 (M+1)$^+$

Example 2

5-(5-acetyl-2-butoxy-3-pyridinyl)-3-ethyl-2-(1-ethvl-3-azetidinyl)-2,6-dihydro-7H-pyrazolo[4,3-d]pyrimidin-7-one The title compound from Preparation 2(a) (120 mg, 0.28 mmol) and cesium carbonate (274 mg, 0.84 mmol) were dissolved in n-butanol (4 ml), and heated at 90° C. under nitrogen with molecular sieves for 96 h. The mixture was then partitioned between water (10 ml) and dichloromethane (10 ml). The organic layer was separated, and the aqueous layer extracted further with dichloromethane (3×15 ml). The combined organic layers were dried (MgSO$_4$), and concentrated in vacuo. The crude product was purified by flash column chromatography (95:5:0.5–90:10:1 ethyl acetate:methanol:0.88 NH$_3$ as eluents), to yield the title compound as a colourless glass (77 mg, 0.18 mmol). m.p. 91.6–93.7° C.

¹H NMR (400 MHz, CDCl₃): δ=1.00–1.05 (m, 6H), 1.38 (t, 3H), 1.50–1.62 (m, 2H), 1.90–2.00 (m, 2H), 2.63 (s, 3H), 2.63–2.70 (m, 2H), 3.02 (q, 2H), 3.75 (t, 2H), 3.90 (t, 2H), 4.68 (t, 2H), 5.10–5.20 (m, 1H), 8.84 (s, 1H), 9.23 (s, 1H), 10.63 (br s,1H).

LRMS (TSP-positive ion) 439 (MH⁺)

Anal. Found C, 60.73; H, 7.06; N, 18.03 Calcd for C₂₃H₃₀O₃N₆.0.2MeOH.0.1 DIPE: C, 60.88; H, 7.26; N, 17.90

Preparation of starting materials for Example 2

2(a) 5-(5-Acetyl-2-propoxy-3-pyridinyl)-3-ethyl-2-(1-ethyl-3-azetidinyl)-2,6-dihydro-7H-pyrazolo[4,3-d]pyrimidin-7-one Sodium cyanoborohydride (92 mg, 1.47 mmol) was added to a stirring solution of title compound from Preparation 2(b) (500 mg, 0.98 mmol), acetaldehyde (64 µl, 1.18 mmol) and sodium acetate (161 mg, 1.96 mmol) in methanol (10 ml) under nitrogen at room temperature. After 1 h the mixture was poured into NaHCO₃ (sat. aq., 20 ml), and extracted with dichloromethane (3×15 ml). The combined organic layers were dried (MgSO₄) and concentrated in vacuo. The crude product was purified by flash column chromatography (95:5:0.5–80:20:1 ethyl acetate:methanol:0.88 NH₃ as eluent) to yield the title compound as a white solid (140 mg, 0.33 mmol).

¹H NMR (400 MHz, CDCl₃): δ=0.97 (t, 3H), 1.03 (t, 3H), 1.30 (t, 3H), 2.82–2.97 (m, 2H), 2.58–2.65 (m, 5H), 2.98 (q, 2H), 3.68 (t, 2H), 3.85 (dd, 2H), 4.58 (dd, 2H), 5.05–5.17 (m, 1H), 8.79 (s, 1H), 9.18 (s, 1H), 10.62 (br s,1H).

LRMS (TSP-positive ion) 426 (MH⁺)

2(b) 5-(5-Acetyl-2-propoxy-3-pyridinyl)-2-(3-azetidinyl)-3-ethyl-2,6-dihydro-7H-pyrazolo[4,3-d]pyrimidin-7-one The title compound of Preparation 2(c) (1.44 g, 3.0 mmol) in acetone (50 ml) and sulphuric acid (1N, 3 ml) was treated with mercuric sulphate (268 mg, 9.0 mmol) and heated to reflux for 6 h. The reaction mixture was concentrated to ~20 ml in vacuo, poured into sodium bicarbonate (sat. aq., 20 ml) and extracted into methylene chloride (6×20 ml). Combined organics were washed with brine (20 ml), dried over MgSO₄, and concentrated to a brown oil which was taken up in 40% trifluoroacetic acid in methylene chloride (50 ml) and water (1 ml) and stirred for 1 h at room temperature. After evaporation in vacuo, the residue was purified by column chromatography (eluting with 95:5:1 methylene chloride:methanol:0.88 ammonia) to afford the title compound as a white hydroscopic foam (1.65 g). m.p. 128.5–130.0° C.

¹H NMR (400 MHz, MeOD): δ=1.00 (t, 3H), 1.30 (t, 3H), 1.79–1.90 (m, 2H), 2.60 (s, 3H), 3.00–3.10 (q, 2H), 4.50 (t, 2H), 4.60–4.70 (m, 4H), 5.65–5.78 (m, 1H), 8.65 (s, 1H), 8.90 (s, 1H)

LRMS (TSP-positive ion) 397 (MH⁺)

2(c) tert-Butyl 3-[3-ethyl-5-(5-ethynyl-2-propoxy-3-pyridinyl)-7-oxo-6,7-dihydro-2H-pyrazolo[4,3-d]pyrimidin-2-yl]-1-azetidinecarboxylate Prepared from the title compound of Preparation 2(d) by the method of Preparation 2(c)(i).

¹H NMR (400 MHz, CDCl₃): δ=1.05 (t, 3H), 1.30 (t, 3H), 1.43 (s, 9H), 1.88–2.00 (m, 2H), 3.00 (q, 2H), 3.19 (s, 1 H), 4.35 (app t, 2H), 4.52 (app t, 2H), 4.60–4.80 (br s, 2H), 5.22 (t, 1 H), 8.39 (s, 1 H), 8.80 (s, 1 H), 10.75 (br s,1H)

LRMS (TSP-positive ion) 496 (MNH₄⁺).

2(c)(i) 5-(2-Butoxy-5-ethynyl-3-pyridinyl)-3-ethyl-2-(2-methoxyethyl)-2,6-dihydro-7H-pyrazolo[4,3-d]pyrimidin-7-one Potassium fluoride (22 mg, 0.38 mmol) was added to a stirred solution of the title compound of Preparation 2(d)(i) (90 mg, 0.19 mmol) in aqueous N,N-dimethylformamide (2 mL N,N-dimethylformamide /0.2 mL water) at 0° C. After 10 min the reaction was allowed to warm to room temperature and stirred for 2 h. The reaction mixture was diluted with ethyl acetate and washed with water, 1 N hydrochloric acid (3 times) and brine. The organic layer was dried (MgSO₄) and concentrated to give the title compound as a white solid (75 mg).

¹H NMR (400 MHz, CDCl₃): δ=1.00 (t, 3H), 1.40 (t, 3H), 1.50 (m, 2H), 1.90 (m, 2H), 3.05 (q, 2H), 3.20 (s, 1 H), 3.30 (s, 3H), 3.85 (t, 2H), 4.40 (t, 2H), 4.60 (t, 2H), 8.40 (s, 1H), 8.80 (s, 1H), 10.70 (s, 1H).

LRMS (TSP): 396.3 (MH⁺).

2(d) tert-Butyl3-(3-ethyl-7-oxo-5-{2-propoxy-5-[(trimethylsilyl)ethynyl]-3-pyridinyl}-6,7-dihydro-2H-pyrazolo[4,3-d]pyrimidin-2-yl)-1-azetidinecarboxylate Prepared from the title compound of Preparation 2(e) by the method of Preparation 2(d)(i).

¹H NMR (400 MHz, MeOD): δ=0.25 (s, 9H), 1.05 (t, 3H), 1.31 (t, 3H), 1.44 (s, 9H), 1.87–1.96 (m, 2H), 3.00 (q, 2H), 4.33 (t, 2H), 4.52 (t, 2H), 4.54–4.80 (m, 2H), 5.18–5.25 (m, 1H), 8.32 (d, 1H), 8.74 (d, 1H)

LRMS (TSP-positive ion) 569 (MNH₄⁺), 552.0 (MH⁺)

Anal. Found C, 60.82; H, 6.90; N, 15.15 Calcd for C₂₈H₃₈O₄N₆Si: C, 61.07; H, 6.95; N, 15.26.

2(d) (i) 5-(2-Butoxy-5-trimethylsilylethynyl-3-pyridinyl)-3-ethyl-2-(2-methoxy-ethyl)-2,6-dihydro-7H-pyrazolo[4,3-d]pyrimidin-7-one The title compound from Example 1 of PCT application IB00/1430 (127 mg, 0.25 mmol) was suspended in triethylamine (2 mL) and trimethylsilylacetylene (38 mg, 0.39 mmol) and acetonitrile (2 mL). Pd(PPh₃)₂Cl₂ (5 mg, 0.006 mmol) and cuprous iodide (1.2 mg, 0.006 mmol) were added and the reaction mixture stirred. After 1 h a further portion of trimethylsilylacetylene (19 mg, 0.19 mmol) was added and stirring continued for 2 h. The solvent was evaporated and the residue partitioned between ethyl acetate and water. The organics were washed with brine, dried (MgSO₄) and concentrated to give a brown foam. Purification by flash column chromatography (gradient elution from 100% dichloromethane to 99% dichloromethane/methanol) gave the title compound as a light brown solid (108 mg).

¹H NMR (300 MHz, CDCl₃): δ=0.25 (s, 9H), 1.00 (t, 3H), 1.40 (t, 3H), 1.50 (m, 2H), 1.90 (m, 2H), 3.10 (q, 2H), 3.30 (s, 3H), 3.90 (t, 2H), 4.40 (t, 2H), 4.60 (t, 2H), 8.40 (s, 1H), 8.80 (s, 1H), 10.70 (s, 1H).

LRMS (TSP): 468.3 (MH⁺).

2(e) tert-Butyl 3-[3-ethyl-5-(5-iodo-2-propoxy-3-pyridinyl)-7-oxo-6,7-dihydro-2H-pyrazolo[4,3-d]pyrimidin-2-yl]-1-azetidinecarboxylate The title compound was prepared from the product of Preparation 2(f) using the method of Preparation 2(e)(i).

¹H NMR (400 MHz, CDCl₃): δ=1.05 (t, 3H), 1.30 (t, 3H), 1.43 (s, 9H), 1.87–1.96 (m, 2H), 3.00 (q, 2H), 4.34 (t, 2H), 4.49 (t, 2H), 4.60 (br s, 2H), 5.20 (t, 1H), 8.41 (d, 1H), 8.94 (s, 1H), 10.75 (br s, 1H)

LRMS (TSP-positive ion) 598.1 ($MNH_4^+$)

Anal. Found C, 47.54; H, 5.02; N, 14.09 Calcd for $C_{23}H_{29}O_4N_6I$: C, 47.60; H, 5.04; N, 14.48.

2(e) (i) 3-Ethyl-5-(5-iodo-2-propoxy-3-pyridinyl)-1-[2-(4-morpholinyl)ethyl]-1,6-dihydro-7H-pyrazolo[4,3-d]pyrimidin-7-one The title compound of Preparation 48 of PCT application IB00/1430 (15.78 g, 28.4 mmol) was dissolved in n-propanol (200 ml), ethyl acetate (6 ml) and potassium t-butoxide (3.2 g, 28.4 mmol) were added and the resultant mixture heated to reflux for 6 h. Additional potassium t-butoxide (1.6 g, 14.2 mmol) was added and the mixture heated for a further 2 h, after which the solvent was removed in vacuo. The residue was partitioned between water (50 ml) and methylene chloride (100 ml) and the organic phase separated. The aqueous phase was extracted with dichloromethane (2×100 ml) and the combined organics dried over $MgSO_4$ and reduced to a yellow solid (~17 g). Purification by column chromatography (elution with ethyl acetate) gave the title compound (13.3 g, 24.1 mmol) together with recovered starting material (2.31 g, 4.2 mmol). m.p. 175–177° C.

$^1$H NMR (300 MHz, $CDCl_3$): δ=1.1 (t, 3H), 1.4 (t, 3H), 1.9–2.05 (m, 2H), 2.45–2.55 (m, 4H), 2.85 (t, 2H), 3.0 (q, 2H), 3.6–3.65 (m, 4H), 4.5 (t, 2H), 4.7 (t, 2H), 8.4 (s, 1H), 9.0 (s, 1H), 10.95 (br s, 1H).

LRMS (TSP) 540 ($MH^+$).

Analysis: found C, 46.79; H, 5.01; N, 15.44. Calcd for $C_{21}H_{27}N_6O_3I$ C, 46.85; H, 5.05; N, 15.61%

2(f) tert-Butyl 3-(3-(aminocarbonyl)-5-ethyl-4-{[(5-iodo-2-propoxy-3-pyridinyl)carbonyl]amino}-1H-pyrazol-1-yl)-1-azetidinecarboxylate The title compound was prepared by the method of Preparation 2(f)(i) using the products from Preparations 2(g) and 2(i).

$^1$H NMR (400 MHz, DMSO): δ=0.95 (t, 3H), 1.05 (t, 3H), 1.40 (s, 9H), 1.78–1.88 (m, 2H), 2.68 (q, 2H), 4.22–4.35 (m, 4H), 4.40 (t, 2H), 5.33 (t, 1H), 7.35 (bs, 1H), 7.52 (bs, 1H), 8.40 (s, 1H), 8.55 (s, 1H), 10.10 (s, 1H)

LRMS (TSP-positive ion) 373.2 ($MH^+$-BOC and I)

Anal. Found C, 45.1 1; H, 5.07; N, 13.56 Calcd for $C_{23}H_{31}O_5N_6I$. 0.2 DCM: C, 45.28; H, 5.14; N, 13.66.

2(f)(i) N-{3-(Aminocarbonyl)-1-[2-dimethylamino)ethyl]-5-ethyl-1H-pyrazol-4-yl}-2-butoxy-5-iodonicotinamide Cesium carbonate (1.17 g, 3.59 mmol) was added to a stirred solution of the title compound from Preparation 16 of PCT application IB00/1430 (800 mg, 1.79 mmol) and N,N-dimethylaminoethyl chloride hydrochloride (309 mg, 2.15 mmol) in N,N-dimethylformamide (10 mL) under a nitrogen atmosphere. The mixture was heated at 80° C. for 24 h. The mixture was cooled and extracted from water with ethyl acetate. The organics were dried ($MgSO_4$) and concentrated to give a brown oil. Purification by flash column chromatography (gradient elution from 100% dichloromethane to 90% dichloromethane/MeOH) gave the product as a pale brown oil (522 mg).

$^1$H NMR (400 MHz, $CDCl_3$): δ=0.95 (t, 3H), 1.20 (t, 3H), 1.40 (m, 2H), 1.90 (m, 2H), 2.35 (s, 6H), 2.80 (t, 2H), 2.85 (q, 2H), 4.20 (t, 2H), 4.60 (t, 2H), 5.30 (br s, 1H), 6.60 (br s, 1H), 8.40 (s, 1H), 8.75 (s, 1H), 10.35 (s, 1H).

LRMS (TSP): 529.5 ($MH^+$).

2(g) N-[3-(Aminocarbonyl)-5-ethyl-1H-pyrazol-4-yl]-5-iodo-2-propoxy-nicotinamide The title compound was prepared from 2-propoxy-5-iodonicotinic acid (see Preparation 2(h) and 4-amino-3-ethyl-1H-pyrazole-5-carboxamide (prepared as described in WO 98/49166) according to the method described in Preparation 2(g)(i).

$^1$H NMR (300 MHz, $d_4$-MeOH): δ=1.0 (t, 3H), 1.25 (t, 3H), 1.85–2.0 (m, 2H), 2.8 (q, 2H), 4.5 (t, 2H), 8.5 (s, 1H), 8.6 (s, 1H).

LRMS (TSP) 444 ($MH^+$).

2(g)(i) N-[3-(Aminocarbonyl)-5-ethyl-1-(2-methoxyethyl)-1H-pyrazol-4-yl]-2-butoxy-5-iodonicotinamide Oxalyl chloride (2 g, 15.9 mmol) was added to a stirred solution of the title compound from Preparation 4 of PCT application IB00/1430 (1.28 g, 3.98 mmol) in dichloromethane (20 mL) and 3 drops N,N-dimethylformamide added. After 2.5 h the solvent was evaporated and the residue azeotroped 3 times with dichloromethane. The residue was resuspended in dichloromethane (4 mL) and added to a stirred mixture of the title compound of Preparation 11 from PCT application IB00/1430 (0.76 g, 3.58 mmol) and triethylamine (0.8 g, 7.97 mmol) in dichloromethane (10 mL). After 1 h the solvent was evaporated and the residue partitioned between ethyl acetate and water. The organic phase was separated and washed with 2 N HCl (twice), sodium bicarbonate solution (twice) and brine before being dried ($MgSO_4$) and concentrated. The product was triturated with ether and filtered to give 820 mg of pure product as a white solid. The mother liquor was concentrated and purified by flash column chromatography (elution with 80% ethyl acetate: hexane), to give a further 605 mg of product.

$^1$H NMR (400 MHz, $CDCl_3$): δ=0.95 (t, 3H), 1.20 (t, 3H), 1.45 (m, 2H), 1.90 (m, 2H), 2.85 (q, 2H), 3.35 (s, 3H), 3.80 (t, 2H), 4.25 (t, 2H), 4.60 (t, 2H), 5.20 (br s, 1H), 6.60 (br s, 1H), 8.40 (s, 1H), 8.80 (s, 1H), 10.30 (s, 1H).

LRMS (TSP): 516.2 ($MH^+$).

2(h) 2-Propoxy-5-iodonicotinic acid

The title compound was prepared from 2-propoxy nicotinic acid (prepared as described in WO 99/54333, the compound 2-n-propoxypyridine-3-carboxylic acid, Preparation 46 prepared by the process of Preparation 1) using the method of Preparation 2(h)(i).

$^1$H NMR (300 MHz, $CDCl_3$): δ=1.05 (t, 3H), 1.85–2.0 (m, 2H), 4.5 (t, 2H), 8.5 (s, 1H), 8.6 (s, 1H).

Analysis: found C, 35.16; H, 3.19; N, 4.46. Calcd for $C_9H_{10}INO_3$: C, 35.19; H, 3.28; N, 4.56%

2(h)(i) 2-isoButoxy-5-iodo nicotinic acid

N-Iodosuccinamide (18.22 g, 0.08 mol), trifluoroacetic acid (100 mL) and trifluoroacetic anhydride (25 mL) were added to 2-isobutoxynicotinic acid (10.55 g, 0.054 mol). The mixture was refluxed for 2.5 h, cooled and the solvents evaporated. The residue was extracted from water with ethyl acetate and the organics washed with water (twice) and brine (twice), dried ($MgSO_4$) and concentrated. The red residue was redissolved in ethyl acetate washed with sodium thiosulfate solution (twice), water (twice), brine (twice), redried (MgSO$_4$) and concentrated to give the desired product as a yellow solid.

$^1$H NMR (300 MHz, CDCl$_3$): δ=1.05 (d, 6H), 2.20 (m, 1H), 4.40 (d, 2H), 8.50 (s,1H), 8.70 (s,1H),

LRMS (TSP): 322.3 (MH$^+$).

2(i) tert-Butyl 3-iodo-1-azetidinecarboxylate

A mixture of tert-butyl 3-[(methylsulfonyl)oxy]-1-azetidinecarboxylate (prepared as described in Synlett 1998, 379; 5.0 g, 19.9 mmol), and potassium iodide (16.5 g, 99.4 mmol) in N,N-dimethylformamide (25 mL), was heated at 100° C. for 42 h. The cooled mixture was partitioned between water and ethyl acetate, and the layers separated. The organic phase was dried over MgSO$_4$, concentrated under reduced pressure and the residue azeotroped with xylene. The crude product was purified by flash column chromatography (dichloromethane as eluant) to give the title compound, 3.26 g.

$^1$H NMR (300 MHz, CDCl$_3$) δ=1.43 (s, 9H), 4.28 (m, 2H), 4.46 (m, 1H), 4.62 (m, 2H).

LRMS (TSP) 284 (MH)$^+$

What we claim is:

1. A process for the production of a pyrazole compound of formula (II)

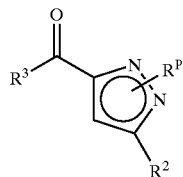

II wherein

R$^P$ is H or R$^1$;

R$^1$ is H, (C$_1$–C$_6$)alkyl, (C$_1$–C$_6$)alkoxy, (C$_3$–C$_6$)cycloalkyl, (C$_1$–C$_6$)alkyl((C$_1$–C$_6$)alkoxy), Het, (C$_1$–C$_6$)alkylHet, aryl, or (C$_1$–C$_6$)alkylaryl, where the latter eight groups are all optionally substituted by one or more substituents selected from the group consisting of halo, cyano, nitro, (C$_1$–C$_6$)alkyl, C(O)NR R$^5$, C(O)R$^6$, C(O)OR$^7$, OR$^8$, NR$^{9a}$R$^{9b}$ and SO$_2$NR$^{10a}$R$^{10b}$;

R$^2$ is (C$_1$–C$_6$)alkyl, (C$_1$–C$_6$)alkoxy, (C$_3$–C$_6$)cycloalkyl, (C$_1$–C$_6$)alkyl((C$_1$–C$_6$)alkoxy), Het, (C$_1$–C$_6$)alkylHet, aryl, or (C$_1$–C$_6$)alkylaryl, where the latter eight groups are all optionally substituted by one or more substituents selected from the group consisting of halo, cyano, nitro, (C$_1$–C$_6$)alkyl, C(O)NR$^4$R$^5$, C(O)R$^6$, C(O)OR$^7$, OR$^8$, NR$^{9a}$R$^{9b}$ and SO$_2$NR$^{10a}$R$^{10b}$;

R$^3$ is OH, (C$_1$–C$_6$)alkoxy, or NR$^4$R$^5$;

R$^4$, R$^5$, R$^6$, R$^7$, R$^8$, R$^{10a}$ and R$^{10b}$ are each independently H or (C$_1$–C$_6$)alkyl;

R$^{9a}$ and R$^{9b}$ are each independently H, (C$_1$–C$_6$)alkyl, or taken together with the nitrogen atom to which they are attached form an azetidinyl, pyrollidinyl, or piperidinyl group; and Het is a fully saturated, partly unsaturated, wholly aromatic, partly aromatic or bicyclic heterocyle, wherein said process comprises the steps of (i) reacting a compound of formula (III),

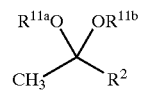

III where R$^{11a}$ and R$^{11b}$ are each independently (C$_1$–C$_6$)alkyl and R$^2$ is as defined herein before, with an acylating agent of the formula (IV) in the presence of a base and an optional activating agent,

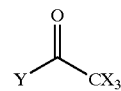

IV where X is a halogen independently selected from Cl, F or Br and where Y is a halogen or OR$^{12}$ where R$^{12}$ is (C$_1$–C$_6$)alkyl, C(O)CX$_3$, Het, or (C$_1$–C$_6$)alkyl(Het), where Het is pyridine or imidazole; and (ii) adding in situ a hydrazine compound of formula (V)

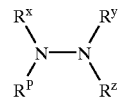

V where R$^P$ is H or R$^1$ where R$^1$ is as defined hereinbefore, and R$^x$, R$^y$ and R$^z$ are each independently selected from H, an electron donating group, or an electron withdrawing group where said electron withdrawing group or said electron donating group is labile under the conditions of the reaction.

2. The process of claim 1 wherein said compound of formula (III) is reacted with at least one equivalent of said acylating agent of formula (IV) in step (i).

3. The process of claim 1 wherein said compound of formula (III) is reacted with at least two equivalents of said acylating agent of formula (IV) in step (i).

4. The process of claim 1 wherein said compound of formula (II) is a compound of formula IIA

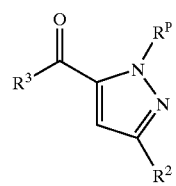

IIA where R$^P$, R$^2$, and R$^3$ are as defined hereinbefore.

5. The process of claim 1 wherein said compound of formula (II) is a compound of formula IIB

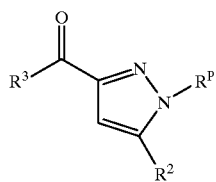

where $R^P$, $R^2$, and $R^3$ are as defined hereinbefore.

6. A process for the production of a pyrazole compound of formula (IIA),

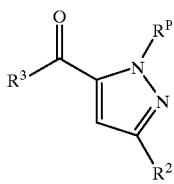

IIA wherein
$R^P$ is H or $R^1$, where $R^1$ is $(C_1–C_4)$alkyl optionally substituted by one or more substituents selected from the group consisting of halo, cyano, nitro, $(C_1–C_6)$alkyl, $C(O)NR^4R^5$, $C(O)R^6$, $C(O)OR^7$, $OR^8$, $NR^{9a}R^{9b}$ and $SO_2N\ R^{10a}R^{10b}$;
$R^2$ is $(C_1–C_4)$alkyl;
$R^3$ is $(C_1–C_3)$alkoxy,
wherein said process comprises the steps of
(i) reacting a compound of formula (III),

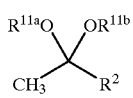

III where $R^{11a}$ and $R^{11b}$ are each independently $(C_1–C_4)$alkyl and $R^2$ is $(C_1–C_4)$alkyl, with an acylating agent of the formula (IV),

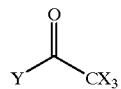

IV where X is Cl or F, and Y is Cl, F or $C(O)CX_3$, in the presence of a base and an optional activating agent; and
(ii) adding in situ a hydrazine compound of formula (V)

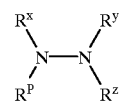

V where $R^P$ is H or $R^1$, where $R^1$ is as defined hereinbefore, and $R^x$=EWG, $R^y$ and $R^z$=H; or $R^x$ and $R^y$=H and $R^z$=EDG; or $R^x$=$R^y$=$R^z$=H when $R^1$=EWG; or $R^x$=EWG, $R^y$=H and $R^z$=EDG, wherein EWG is a tri$(C_1–C_2)$alkylsilyl group and EDG is tert-butyloxycarbonyl or trifluoroacetamide.

7. The process of claim 6 wherein said compound of formula (III) is reacted with at least one equivalent of said acylating agent of formula (IV) in step (i).

8. The process of claim 6 wherein said compound of formula (III) is reacted with at least two equivalents of said acylating agent of formula (IV) in step (i).

9. A process for the production of a pyrazole compound of formula (IIB),

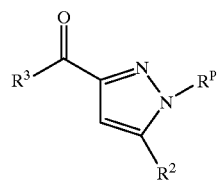

IIB wherein
$R^P$ is H or $R^1$, where $R^1$ is $(C_1–C_4)$alkyl or $(C_1–C_4)$alkyl$((C_1–C_2)$ alkoxy);
$R^2$ is $(C_1–C_4)$alkyl; and
$R^3$ is $(C_1–C_3)$alkoxy,
wherein said process comprises the steps of
(i) reacting a compound of formula (III)

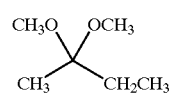

III with an acylating agent of formula (IV) in the presence of pyridine and an optional activating agent

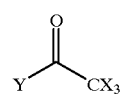

IV where X and Y are each independently Cl or F; and
(ii) adding after about 8 hours to about 24 hours a hydrazine compound of formula (V)

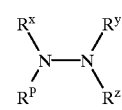

V where $R^P$ is H when
$R^x$=EWG, $R^y$ and $R^z$=H; or
$R^x$ and $R^y$=H and $R^z$=EDG; or
$R^x$=$R^y$=$R^z$=H when $R^z$=EWG; or
$R^x$=EWG, $R^y$=H and $R^z$=EDG, where EDG is a tri$(C_1–C_2)$alkylsilyl group and EWG is tert-butyloxycarbonyl or trifluoroacetamide;

and $R^P$ is $R^1$, where $R^1$ is as defined hereinbefore, when $R^x$=H, $R^{y=H\ and\ Rz}$=EWG; or $R^x$=EDG, $R^y$=H and $R^z$=H; or $R^x$=$R^y$=$R^z$=H when $R^1$=EDG; or $R^x$=EDG, $R^y$=H and $R^z$=EWG, where EDG is a tri($C_1$–$C_2$)alkylsilyl group and EWG is tert-butyloxycarbonyl or trifluoroacetamide.

10. The process of claim 9 wherein said compound of formula (III) is reacted with at least one equivalent of said acylating agent of formula (IV) in step (i).

11. The process of claim 9 wherein said compound of formula (III) is reacted with at least two equivalents of said acylating agent of formula (IV) in step (i).

* * * * *